(12) United States Patent
Rafiee et al.

(10) Patent No.: US 10,058,315 B2
(45) Date of Patent: Aug. 28, 2018

(54) DEVICES AND METHODS FOR CLOSURE OF TRANSVASCULAR OR TRANSCAMERAL ACCESS PORTS

(71) Applicants: TRANSMURAL SYSTEMS LLC, Andover, MA (US); THE UNITED STATES OF AMERICA, AS REPRESENTED BY THE SECRETARY, Washington, DC (US)

(72) Inventors: Nasser Rafiee, Andover, MA (US); Stuart MacDonald, Andover, MA (US); Robert J. Lederman, Chevy Chase, MD (US); Toby Rogers, Bethesda, MD (US); Rany Busold, Andover, MA (US); Koosha Rafiee, Andover, MA (US)

(73) Assignees: Transmural Systems LLC, Andover, MA (US); The United States of America, as represented by the Secretary, Department of Health and Human Services, Washington, DC (US)

( * ) Notice: Subject to any disclaimer, the term of this patent is extended or adjusted under 35 U.S.C. 154(b) by 132 days.

(21) Appl. No.: 15/277,798

(22) Filed: Sep. 27, 2016

(65) Prior Publication Data
US 2017/0014114 A1 Jan. 19, 2017

Related U.S. Application Data

(63) Continuation-in-part of application No. PCT/US2015/022782, filed on Mar. 26, 2015.
(Continued)

(51) Int. Cl.
*A61B 17/00* (2006.01)
*A61B 17/12* (2006.01)
*A61B 90/00* (2016.01)

(52) U.S. Cl.
CPC .... *A61B 17/0057* (2013.01); *A61B 17/12031* (2013.01); *A61B 17/12109* (2013.01);
(Continued)

(58) Field of Classification Search
CPC ...... A61B 17/12031; A61B 2017/1205; A61B 17/1214; A61B 17/12109;
(Continued)

(56) References Cited

U.S. PATENT DOCUMENTS

| 4,106,129 A | 8/1978 | Carpentier et al. |
| 4,259,753 A | 4/1981 | Liotta et al. |

(Continued)

FOREIGN PATENT DOCUMENTS

| EP | 2412397 A1 | 2/2012 |
| RU | 100 718 U1 | 12/2010 |

(Continued)

OTHER PUBLICATIONS

International Search Report, for related application No. PCT/US2011/059586, dated May 25, 2012.
(Continued)

*Primary Examiner* — Katrina Stransky
(74) *Attorney, Agent, or Firm* — Crawford Maunu PLLC

(57) ABSTRACT

The present disclosure provides a variety of prostheses, delivery systems and techniques to facilitate closure of transvascular or transcameral access ports. Various embodiments of prostheses are provided including a plurality of radially expandable mesh discs filled with material to facilitate coagulation and to reduce or stop leakage from punctures in vessel walls.

13 Claims, 26 Drawing Sheets

Related U.S. Application Data

(60) Provisional application No. 61/971,458, filed on Mar. 27, 2014, provisional application No. 62/083,192, filed on Nov. 22, 2014, provisional application No. 62/326,710, filed on Apr. 23, 2016.

(52) U.S. Cl.
CPC ........... *A61B 2017/00243* (2013.01); *A61B 2017/00557* (2013.01); *A61B 2017/00575* (2013.01); *A61B 2017/00592* (2013.01); *A61B 2017/00597* (2013.01); *A61B 2017/00601* (2013.01); *A61B 2017/00606* (2013.01); *A61B 2017/00623* (2013.01); *A61B 2017/00641* (2013.01); *A61B 2017/00964* (2013.01); *A61B 2017/1205* (2013.01); *A61B 2090/3966* (2016.02)

(58) Field of Classification Search
CPC ........... A61B 2017/00964; A61B 2017/00641; A61B 2017/00623; A61B 2017/00606; A61B 2017/00601; A61B 2017/00597; A61B 2017/00592; A61B 2017/00575; A61B 2017/00557; A61B 17/0057; A61B 2017/00247; A61B 2017/00991; A61B 17/12122; A61B 17/1215; A61B 17/12145; A61F 2230/0091; A61F 2250/0098
See application file for complete search history.

(56) References Cited

U.S. PATENT DOCUMENTS

| | | |
|---|---|---|
| 4,666,442 A | 5/1987 | Arru et al. |
| 4,692,164 A | 9/1987 | Dzemeshkevich et al. |
| 5,411,552 A | 5/1995 | Andersen et al. |
| 5,449,384 A | 9/1995 | Johnson |
| 5,606,928 A | 3/1997 | Religa et al. |
| 5,788,715 A | 8/1998 | Watson, Jr. et al. |
| 5,861,028 A | 1/1999 | Angell |
| 5,895,410 A | 4/1999 | Forber et al. |
| 5,928,281 A | 7/1999 | Huynh et al. |
| 6,059,769 A | 5/2000 | Lunn et al. |
| 6,106,510 A | 8/2000 | Lunn et al. |
| 6,375,774 B1 | 4/2002 | Lunn et al. |
| 6,599,303 B1 | 7/2003 | Peterson |
| 6,602,271 B2 | 8/2003 | Adams et al. |
| 6,716,231 B1 | 4/2004 | Rafiee et al. |
| 6,733,525 B2 | 5/2004 | Yang et al. |
| 6,790,229 B1 | 9/2004 | Berreklouw |
| 6,797,000 B2 | 9/2004 | Simpson et al. |
| 6,800,081 B2 | 10/2004 | Parodi |
| 6,866,677 B2 | 3/2005 | Douk et al. |
| 6,911,036 B2 | 6/2005 | Douk et al. |
| 6,953,476 B1 | 10/2005 | Shalev |
| 6,960,217 B2 | 11/2005 | Bolduc |
| 7,044,958 B2 | 5/2006 | Douk et al. |
| 7,066,946 B2 | 6/2006 | Douk et al. |
| 7,189,259 B2 | 3/2007 | Simionescu et al. |
| 7,195,641 B2 | 3/2007 | Palmaz et al. |
| 7,201,772 B2 | 4/2007 | Schwammenthal et al. |
| 7,294,135 B2 | 11/2007 | Stephens et al. |
| 7,316,706 B2 | 1/2008 | Bloom et al. |
| 7,399,315 B2 | 7/2008 | Iobbi |
| 7,425,219 B2 | 9/2008 | Quadri |
| 7,442,204 B2 | 10/2008 | Schwammenthal et al. |
| 7,442,207 B2 | 10/2008 | Rafiee |
| 7,445,631 B2 | 11/2008 | Salahieh et al. |
| 7,481,838 B2 | 1/2009 | Carpentier et al. |
| 7,491,232 B2 | 2/2009 | Bolduc et al. |
| 7,524,330 B2 | 4/2009 | Berreklouw |
| 7,655,040 B2 | 2/2010 | Douk et al. |
| 7,682,352 B2 | 3/2010 | Rafiee et al. |
| 7,699,892 B2 | 4/2010 | Rafiee et al. |
| 7,716,801 B2 | 5/2010 | Douk et al. |
| 7,753,840 B2 | 7/2010 | Simionescu et al. |
| 7,753,949 B2 | 7/2010 | Lamphere et al. |
| 7,780,726 B2 | 8/2010 | Seguin |
| 7,799,069 B2 | 9/2010 | Bailey et al. |
| 7,806,917 B2 | 10/2010 | Xiao |
| 7,806,919 B2 | 10/2010 | Bloom et al. |
| 7,815,673 B2 | 10/2010 | Bloom et al. |
| 7,947,072 B2 | 5/2011 | Yang et al. |
| 7,955,384 B2 | 6/2011 | Rafiee et al. |
| 7,972,370 B2 | 7/2011 | Douk et al. |
| 7,998,188 B2 | 8/2011 | Zilla et al. |
| 8,002,825 B2 | 8/2011 | Letac et al. |
| 8,052,750 B2 | 11/2011 | Tuval et al. |
| 8,062,355 B2 | 11/2011 | Figulla et al. |
| 8,070,802 B2 | 12/2011 | Lamphere et al. |
| 8,092,518 B2 | 1/2012 | Schreck |
| 8,092,520 B2 | 1/2012 | Quadri |
| 8,092,524 B2 | 1/2012 | Nugent et al. |
| 8,226,710 B2 | 7/2012 | Nguyen et al. |
| 8,252,051 B2 | 8/2012 | Chau et al. |
| 8,308,798 B2 | 11/2012 | Pintor et al. |
| 8,337,541 B2 | 12/2012 | Quadri et al. |
| 8,348,995 B2 | 1/2013 | Tuval et al. |
| 8,348,996 B2 | 1/2013 | Tuval et al. |
| 8,353,954 B2 | 1/2013 | Cai et al. |
| 8,353,955 B2 | 1/2013 | Styrc et al. |
| 2001/0021872 A1 | 9/2001 | Bailey et al. |
| 2002/0032481 A1 | 3/2002 | Gabbay |
| 2002/0138138 A1 | 9/2002 | Yang |
| 2003/0055495 A1 | 3/2003 | Pease et al. |
| 2003/0057156 A1 | 3/2003 | Peterson et al. |
| 2003/0065386 A1 | 4/2003 | Weadock |
| 2003/0097172 A1 | 5/2003 | Shalev et al. |
| 2004/0087998 A1 | 5/2004 | Lee et al. |
| 2004/0127916 A1 | 7/2004 | Bolduc et al. |
| 2005/0038508 A1 | 2/2005 | Gabbay |
| 2005/0043790 A1 | 2/2005 | Seguin |
| 2005/0055082 A1 | 3/2005 | Ben-Muvhar et al. |
| 2005/0137769 A1 | 6/2005 | Salahieh et al. |
| 2005/0143809 A1 | 6/2005 | Salahieh et al. |
| 2005/0177180 A1 | 8/2005 | Kaganov et al. |
| 2005/0273135 A1* | 12/2005 | Chanduszko ...... A61B 17/0057 606/213 |
| 2005/0288706 A1 | 12/2005 | Widomski et al. |
| 2006/0085012 A1 | 4/2006 | Dolan |
| 2006/0106449 A1 | 5/2006 | Ben-Muvhar |
| 2006/0106450 A1 | 5/2006 | Ben-Muvhar |
| 2006/0155303 A1 | 7/2006 | Konya et al. |
| 2006/0167494 A1* | 7/2006 | Suddaby ............ A61B 17/0057 606/213 |
| 2006/0173537 A1 | 8/2006 | Yang et al. |
| 2007/0010851 A1* | 1/2007 | Chanduszko ...... A61B 17/0057 606/213 |
| 2007/0043435 A1 | 2/2007 | Seguin et al. |
| 2007/0067029 A1 | 3/2007 | Gabbay |
| 2007/0250160 A1 | 10/2007 | Rafiee |
| 2007/0255398 A1 | 11/2007 | Yang et al. |
| 2007/0288089 A1 | 12/2007 | Gurskis et al. |
| 2007/0293942 A1 | 12/2007 | Mizraee |
| 2008/0015687 A1 | 1/2008 | Lashinski et al. |
| 2008/0021537 A1 | 1/2008 | Ben-Muvhar et al. |
| 2008/0033475 A1 | 2/2008 | Meng |
| 2008/0065191 A1 | 3/2008 | Bolduc et al. |
| 2008/0077234 A1 | 3/2008 | Styrc |
| 2008/0125860 A1 | 5/2008 | Webler et al. |
| 2008/0208328 A1 | 8/2008 | Antocci et al. |
| 2008/0221672 A1 | 9/2008 | Lamphere et al. |
| 2009/0005863 A1 | 1/2009 | Goetz et al. |
| 2009/0062841 A1 | 3/2009 | Amplatz et al. |
| 2009/0270966 A1 | 10/2009 | Douk et al. |
| 2009/0270976 A1 | 10/2009 | Douk et al. |
| 2009/0306768 A1 | 12/2009 | Quadri |
| 2009/0319038 A1 | 12/2009 | Gurskis et al. |
| 2010/0036479 A1 | 2/2010 | Hill et al. |
| 2010/0082094 A1 | 4/2010 | Quadri et al. |
| 2010/0100167 A1 | 4/2010 | Bortlein et al. |
| 2010/0174363 A1 | 7/2010 | Castro |

(56) References Cited

U.S. PATENT DOCUMENTS

| | | |
|---|---|---|
| 2010/0179648 A1 | 7/2010 | Richter et al. |
| 2010/0179649 A1 | 7/2010 | Richter et al. |
| 2010/0185275 A1 | 7/2010 | Richter et al. |
| 2010/0211046 A1 | 8/2010 | Adams et al. |
| 2010/0249923 A1 | 9/2010 | Alkhatib et al. |
| 2010/0262232 A1 | 10/2010 | Annest |
| 2010/0280606 A1 | 11/2010 | Naor |
| 2010/0298931 A1 | 11/2010 | Quadri et al. |
| 2011/0112632 A1 | 5/2011 | Chau et al. |
| 2011/0137409 A1 | 6/2011 | Yang et al. |
| 2011/0172784 A1 | 7/2011 | Richter et al. |
| 2011/0282438 A1 | 11/2011 | Drews et al. |
| 2011/0313515 A1 | 12/2011 | Quadri et al. |
| 2011/0319988 A1 | 12/2011 | Schankereli et al. |
| 2011/0319989 A1 | 12/2011 | Lane et al. |
| 2012/0022639 A1 | 1/2012 | Hacohen |
| 2012/0059450 A1 | 3/2012 | Chiang et al. |
| 2012/0078353 A1 | 3/2012 | Quadri et al. |
| 2012/0078360 A1 | 3/2012 | Rafiee |
| 2012/0179244 A1 | 7/2012 | Schankereli et al. |
| 2012/0215303 A1 | 8/2012 | Quadri et al. |
| 2012/0283768 A1 | 11/2012 | Cox et al. |
| 2012/0316642 A1 | 12/2012 | Yu et al. |
| 2012/0323316 A1 | 12/2012 | Chau et al. |
| 2013/0282054 A1* | 10/2013 | Osypka ............... A61B 17/0057 606/213 |
| 2013/0289618 A1 | 10/2013 | Chanduszko et al. |
| 2014/0018906 A1 | 1/2014 | Rafiee |
| 2014/0128965 A1 | 5/2014 | Rafiee |
| 2014/0163608 A1* | 6/2014 | Osypka ............... A61N 1/0587 606/213 |
| 2014/0163668 A1 | 6/2014 | Rafiee |
| 2014/0257361 A1* | 9/2014 | Prom ............... A61B 17/12022 606/198 |
| 2014/0257373 A1* | 9/2014 | Prom ............... A61B 17/12022 606/213 |
| 2014/0358223 A1 | 12/2014 | Rafiee et al. |
| 2014/0039083 A1 | 2/2015 | Rafiee |

FOREIGN PATENT DOCUMENTS

| | | |
|---|---|---|
| WO | 9939646 A1 | 8/1999 |
| WO | WO2007121314 A2 | 10/2007 |
| WO | WO2012061809 A2 | 5/2012 |
| WO | WO2013131069 A1 | 9/2013 |
| WO | 2013159065 A1 | 10/2013 |
| WO | WO2015069947 A1 | 5/2015 |
| WO | WO2015148821 A1 | 10/2015 |

OTHER PUBLICATIONS

International Preliminary Report on Patentability and Written Opinion, or related application No. PCT/US2011/059586, dated May 25, 2012.

BioIntegral Surgical, Mitral Valve Restoration System.

International Search Report for co-pending international application No. PCT/US2013/028774, dated Jun. 14, 2013.

International Preliminary Report on Patentability and Written Opinion, on related application No. PCT/US2014/064431 dated Mar. 26, 2015.

International Search Report, for related application No. PCT/US2015/022782, dated Jun. 18, 2015.

EPO. Supplementary European Search Report dated Nov. 3, 2017, for related European Patent Application No. 15768518.1, 2 pages.

* cited by examiner

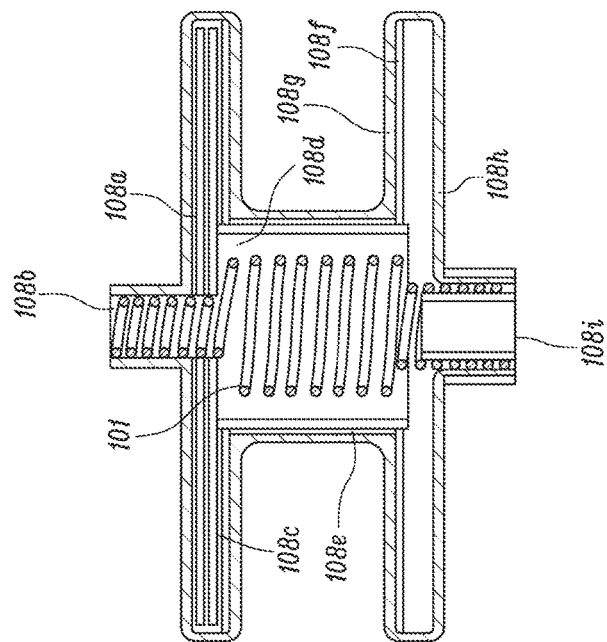
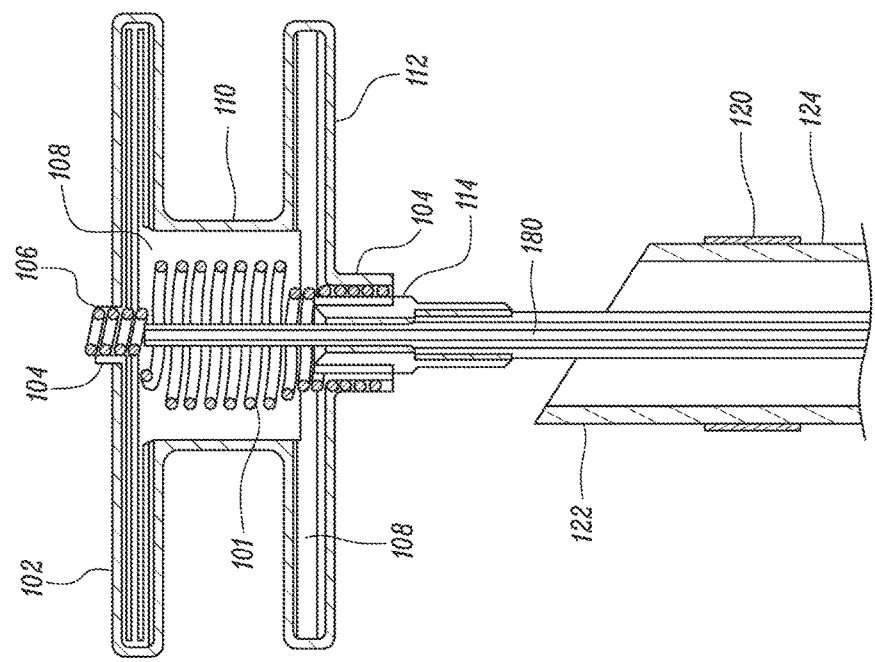
FIG. 1D
FIG. 1C

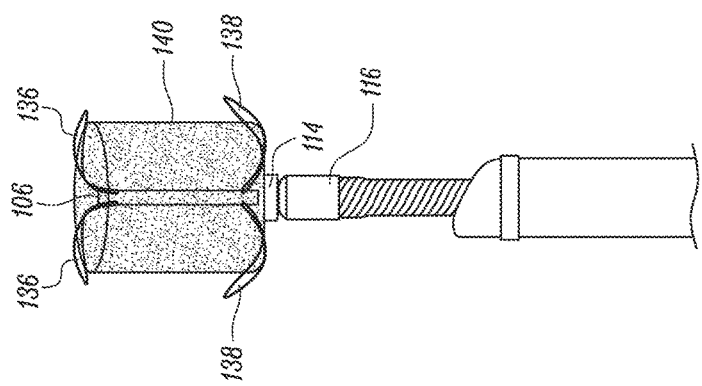

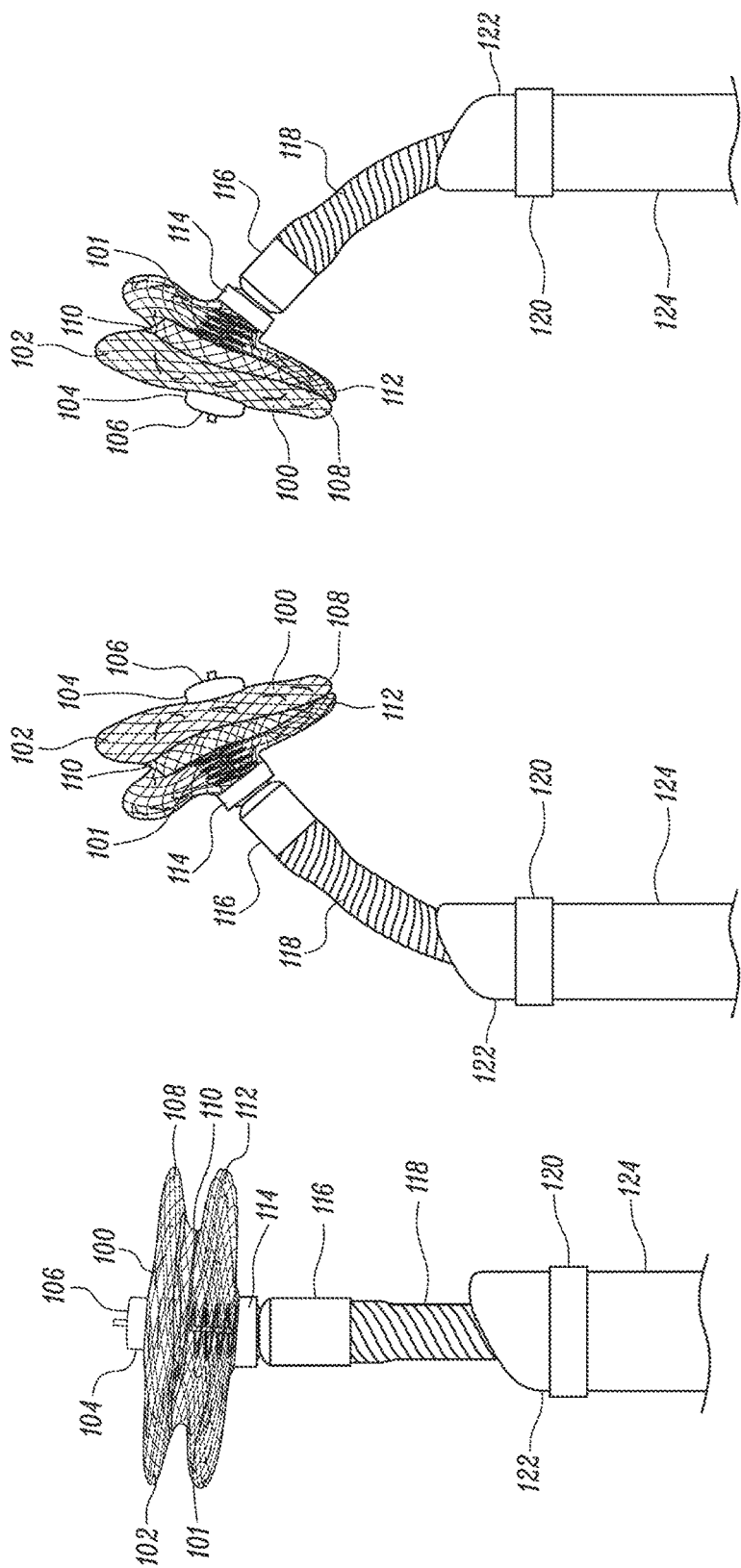

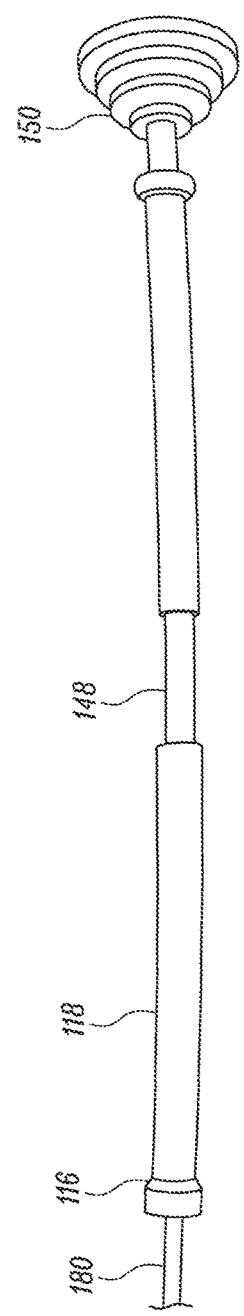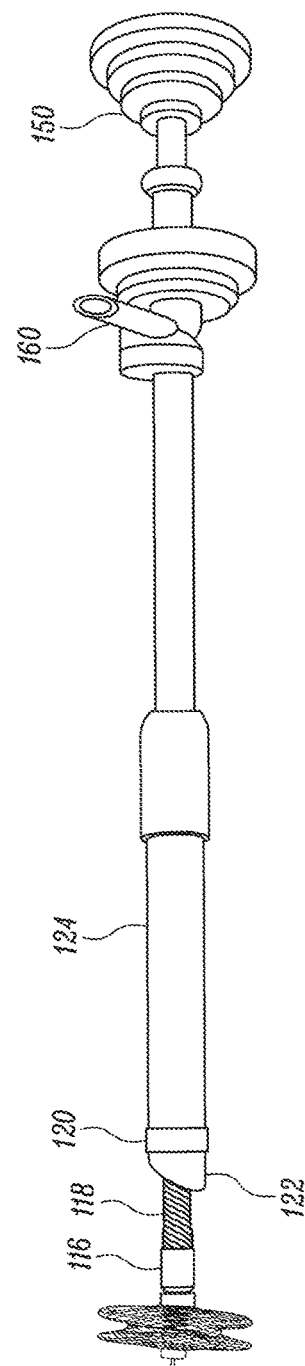
FIG. 7
FIG. 8

DEVICES AND METHODS FOR CLOSURE OF TRANSVASCULAR OR TRANSCAMERAL ACCESS PORTS

CROSS-REFERENCE TO RELATED APPLICATIONS

This patent application is a continuation in part of and claims the benefit of priority to International Application No. PCT/US2015/022782, designating the United States of America, filed Mar. 26, 2015, which in turn claims the benefit of priority to U.S. Provisional Patent Application Ser. No. 61/971,458, filed Mar. 27, 2014 and U.S. Provisional Patent Application Ser. No. 62/083,192, filed Nov. 22, 2014. This patent application also claims the benefit of priority to U.S. Provisional Patent Application Ser. No. 62/326,710, filed Apr. 23, 2016. Each of the foregoing patent applications is incorporated by reference herein in its entirety for any purpose whatsoever.

FEDERALLY-SPONSORED RESEARCH AND DEVELOPMENT

This invention was made with Government support under contract no. 268201500012C awarded by the National Institutes of Health. The U.S. Government has certain rights in the invention.

BACKGROUND

Field of the Disclosure

The present disclosure relates to a device and method for transcatheter correction of cardiovascular abnormalities, such as the delivery of prosthetic valves to the heart. The present disclosure further relates to implants for closing a caval-aortic iatrogenic fistula created by the introduction of a transcatheter device from the inferior vena cava into the abdominal aorta.

Description of Related Art

Transcatheter procedures have been a milestone advance in modern medicine. Percutaneous or transthoracic catheters are advanced through the vascular system or other natural luminal orifices to effect mechanical remodeling through angioplasty or to effect occlusion or patency or valvular function through implants of self-expanding or balloon-expanding occluders, stents, and valves. These procedures can take the place of surgical repair in selected patients.

Percutaneous vascular occluders are limited because usually they require the operator to forego guidewire access between target chambers. Recent innovations permit vascular occluders to be engineered around a central guidewire lumen to enhance safety and versatility of the occluder procedure.

Recently, Halabi and colleagues (JACC 2013; 61:1745), and thereafter Greenbaum and colleagues (Transcatheter therapeutics conference, San Francisco, 2013) reported a novel procedure to introduce large vascular devices into the aorta from the adjoining inferior vena cava. This enabled transcatheter aortic valve replacement in patients otherwise ineligible because of no surgical access to the thorax and insufficient iliofemoral artery caliber. The "caval-aortic" access port, as it is called, was closed using nitinol occluder devices marketed by St Jude Medical (Amplatzer muscular ventricular septal defect occluder or Amplatzer duct occluder) to close congenital cardiovascular defects. These devices are inadequately hemostatic, do not allow uninterrupted guidewire access, and are imperfectly suited for this application.

Transcatheter structural left heart procedures are generally performed through the femoral artery. However, femoral artery caliber or intravascular disease precludes or complicates vascular access in a significant minority of candidates for transcatheter aortic valve replacement or aortic endograft therapy. Moreover, the most frequent life-threatening complication of TAVR is vascular complications of large introducer sheaths placed in the femoral artery. Alternative transcatheter approaches to the heart would therefore be desirable. The present disclosure provides solutions for these and other problems as described herein.

SUMMARY OF THE DISCLOSURE

The purpose and advantages of the present disclosure will be set forth in and become apparent from the description that follows. Additional advantages of the disclosed embodiments will be realized and attained by the methods and systems particularly pointed out in the written description hereof, as well as from the appended drawings.

To achieve these and other advantages and in accordance with the purpose of the disclosure, as embodied herein, in one aspect, the disclosure includes embodiments that solve problems of caval aortic access based on considerable pre-clinical, animal, imaging, and clinical experience in caval-aortic access. These approaches differ substantially from the aforementioned prior art.

In certain embodiments, the problem of variable distance between aortic and caval access points is solved using a telescopic design as disclosed herein. The problem of inadequate hemostasis of aortic and caval access tracts, in some implementations, is solved using "billowing" nitinol weave to fill the vascular holes and by using multiple disks to occlude each vascular rent.

In some implementations, a prosthesis is provided that can include a radially expandable mesh body that is configured to self-expand into at least one disc after becoming radially unconstrained, the radially expandable mesh body defining a volume therein when expanded. The prosthesis can further include a resilient member disposed within the mesh that is attached to a proximal end and distal end of the prosthesis along an axis that defines a central region of the prosthesis. The resilient member can be configured to cause the prosthesis to shorten along the axis and expand radially when the resilient member is relaxed.

The prosthesis can include a material disposed within the mesh that is configured to encourage coagulation when exposed to blood. For example, the material disposed within the mesh can include first and second fabric discs that are disposed within the at least one disc of the radially expandable mesh body to line the radially expandable mesh body with fabric. If desired, the prosthesis can further include a tubular fabric portion attached to at least one of the fabric discs. The tubular fabric portion can extend proximally into a neck region of the prosthesis.

In some implementations, the resilient member can be a coil spring that causes the prosthesis to collapse axially and the at least one disc to expand radially to prevent the prosthesis from being pulled axially through an opening it has been inserted through after it has been deployed. The resilient member can be a tension coil spring, among other materials. The coil spring can include at least two sections of different diameter. If desired, the coil spring can include at least three sections of different diameter. In some implementations, the coil spring can include at least three sections wherein each section has a diameter different than an adjacent section. If desired, the coil spring can include an enlarged central section for causing a neck portion of the prosthesis to bulge radially outwardly when the prosthesis is deployed.

If desired, the radially expandable mesh body can be configured to self-expand into at least two discs connected by the neck region after becoming radially unconstrained. A first disc of the two discs can be configured to mitigate high pressure leaks in an artery. A second disc of the two discs can be configured to mitigate low pressure leaks originating from a vein. The neck region can be configured to cooperate with the first and second discs to prevent leakage from the artery and the vein. At least one of the discs can include a plurality of radially oriented struts attached to the mesh of the at least one disc to enhance the axial compressibility of the prosthesis. The prosthesis can include one or more radially oriented struts attached to the discs at the distal and proximal faces of the prosthesis, that can extend from a radially central portion of the prosthesis to an outer periphery of the prosthesis.

Thus, in some embodiments, the disclosure provides a system for delivering a prosthesis. The system can include one or more of an outer tubular sheath having a proximal end and a distal end and defining a first lumen therethrough along its length, an intermediate tubular member disposed at least partially within the first lumen, and having a proximal end and a distal end and defining a second lumen therethrough along its length. The system can include an inner elongate member disposed at least partially within the second lumen, and having a proximal end and a distal end. The system can further include a prosthesis removably mounted on the distal end of the intermediate tubular member. The prosthesis can include a radially expandable mesh body that is configured to self-expand into at least one disc after becoming radially unconstrained, the radially expandable mesh body defining a volume therein when expanded. The prosthesis can further include a resilient member disposed within the mesh that is attached to a proximal end and distal end of the prosthesis along an axis that defines a central region of the prosthesis. The resilient member can be configured to cause the prosthesis to shorten along the axis and expand radially when the resilient member is relaxed. Distal movement of the inner tubular member against a portion of the prosthesis can cause it to collapse radially and elongate axially so as to permit the prosthesis to be collapsed after deployment, adjusted and redeployed or retracted into the outer tubular member and removed.

If desired, the inner elongate member can be a tubular member, such as a hypotube or polymeric tubular member or composite tubular member configured to permit a guidewire to pass therethrough. The resilient member can be a coil spring, that causes the prosthesis to collapse axially and the at least one disc to expand radially to prevent the prosthesis from being pulled axially through an anatomical opening it has been delivered through after it has been deployed.

In some implementations, the resilient member can be a tension coil spring, among other alternatives such as an elastic material or other resilient material that regains some or all of its original length after being elongated axially. In some implementations, a distal end of the outer tubular member can be cut at an angle that is oblique with respect to a central axis defined by the system. The system can include a steering mechanism to articulate the distal end of the outer tubular member, such that the oblique cut of the distal end of the outer tubular member can facilitate navigation of the distal end of the system, such as through a caval-aortic iatrogenic fistula created by the introduction of a transcatheter device from the inferior vena cava into the abdominal aorta.

If desired, the coil spring can include an enlarged central section for causing the neck portion of the prosthesis to bulge radially outwardly when the prosthesis is deployed. In some implementations, the radially expandable mesh body can be configured to self-expand into at least two discs connected by the neck region after becoming radially unconstrained. A first disc of the two discs can be configured to mitigate high pressure leaks in an artery. A second disc of the two discs can be configured to mitigate low pressure leaks originating from a vein. If desired, the neck region can be configured to cooperate with the first and second discs to prevent leakage from the artery and the vein. In some implementations, the prosthesis can include a material disposed within the mesh that is configured to encourage coagulation when exposed to blood.

The disclosure further provides various prostheses including a radially expandable mesh body that is configured to self-expand into at least one disc after becoming radially unconstrained, the radially expandable mesh body defining a volume therein when expanded. The prosthesis further includes at least one tether attached to the radially expandable mesh body that is configured to cause the radially expandable mesh body to collapse radially when tension is applied to the at least one tether.

If desired, the radially expandable mesh body can be configured to self-expand into at least two discs connected by a neck region after becoming radially unconstrained. A first disc of the two discs can be configured to mitigate high pressure leaks in an artery. A second disc of the two discs can be configured to mitigate low pressure leaks originating from a vein. The neck region can be configured to cooperate with the first and second discs to prevent leakage from the artery and the vein.

In some implementations, the radially expandable mesh body can be configured to self-expand into at least three discs connected by two neck regions after becoming radially unconstrained. A first disc of the two discs can be configured to mitigate high pressure leaks in an artery. A second disc of the two discs can be configured to mitigate low pressure leaks originating from a vein. The neck region can be configured to cooperate with the first and second discs to prevent leakage from the artery and the vein.

If desired, the radially expandable mesh body can be configured to self-expand into at least four discs connected by three neck regions after becoming radially unconstrained. A first disc of the two discs can be configured to mitigate high pressure leaks in an artery. A second disc of the two discs can be configured to mitigate low pressure leaks originating from a vein. The neck region can be configured to cooperate with the first and second discs to prevent leakage from the artery and the vein. If desired, the at least one tether can be threaded through all of the discs to cause all of the discs to collapse radially inwardly upon applying sufficient tension to the at least one tether. In some implementations, the prosthesis can include a material disposed within the mesh that is configured to encourage coagulation when exposed to blood.

In further accordance with the disclosure, any prosthesis disclosed herein can be formed at least in part from a composite wire. In some embodiments, the composite wire can be drawn filled wire. For example, the drawn filled wire can include a first material, and a second material in a different region of the drawn filled wire that has greater radiopacity than the first material. The first and second materials can include metallic components and/or bioresorbable components. If desired, the second material can be located along a core region of the wire, and first material can surround or substantially surround the first material. The first material can include a NiTi alloy, and the second material can include platinum, for example.

In further implementations, the disclosure provides an implantable prosthesis that includes an inflatable bioresorbable body having a proximal end and a distal end, the body being configured to be expanded radially by directing fluid into the body. The prosthesis further can include at least one radially expandable strut attached to each of the proximal end and distal end of the body. Each of the struts can be configured to expand outwardly to prevent the prosthesis from being pulled through an anatomical opening into which it has been inserted.

If desired, the aforementioned prosthesis can further include a coupling located at the proximal end of the prosthesis configured to be attached to a delivery system. The coupling can be configured to permit inflation fluid to pass therethrough.

In a further embodiment, a prosthesis is provided as described herein having a mesh body that is configured to self-expand into at least two discs connected by a neck region after becoming radially unconstrained. A first disc of the at least two discs can be configured to mitigate leaks, and a second disc of the at least two discs can be configured to cause appropriate positioning of the prosthesis in the presence of cardiovascular motion. Such a prosthesis can be used, for example, to address high pressure leaks from an artery or a cardiac chamber. In some implementations, such a prosthesis can be used to address a ventricular septal defect (VSD) (i.e., a hole in the heart). This is a common heart defect that's present at birth (congenital). The hole occurs in the wall that separates the heart's lower chambers (septum) and allows blood to pass from the left to the right side of the heart. The oxygen-rich blood then gets pumped back to the lungs instead of out to the body, causing the heart to work harder. The prosthesis can be delivered and deployed into the defect and deployed, sealing the hole.

In further embodiments, such a prosthesis can be used for various transcardiac applications, wherein the second disk assures retention in position of the prosthesis. For example, such a prosthesis can be used to seal an access opening through the aortic arch that is formed for accessing the aortic valve after the valve is replaced. Similarly, such an approach can be used to seal openings formed in lumenal or vascular walls such as apical access procedures for sealing openings formed through the ventricular wall, for sealing openings formed in a septum (e.g., patent foramen ovale (PFO)) and the like.

Unique benefits of the disclosed prosthesis and delivery system include that the prosthesis can be adjusted, or even removed after being installed in a vascular opening, for any desired reason. Thus, in some embodiments, the disclosure provides a method that includes a delivery system as described herein including a prosthesis as disclosed herein mounted thereon, delivering the delivery system over a guidewire routed to a target location, and fully deploying the prosthesis at the target location to obstruct a vascular opening to be sealed. The prosthesis can then be detached from the delivery system. The delivery system can then be withdrawn over the guidewire after the prosthesis has been detached therefrom. Then, if desired, the delivery system can be once again advanced over the guidewire after withdrawing it, and the prosthesis can be reattached to the delivery system. A further step can then be performed with the prosthesis including at least one of: (i) partially collapsing the prosthesis, (ii) repositioning the prosthesis, and (iii) collapsing and withdrawing the prosthesis into the delivery system, and removing the delivery system and prosthesis over the guidewire. The disclosed method is facilitated by the use of a pushrod (preferably a tubular pushrod) as disclosed herein.

It is to be understood that both the foregoing general description and the following detailed description are exemplary and are intended to provide further explanation of the embodiments disclosed herein.

The accompanying drawings, which are incorporated in and constitute part of this specification, are included to illustrate and provide a further understanding of the method and system of the disclosure. Together with the description, the drawings serve to explain the principles of the disclosed embodiments.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIGS. 1A-1D depict a distal portion of an illustrative delivery system for delivery of a prosthesis for closure of transvascular or transcameral access ports and the prosthesis itself.

FIG. 4D illustrates a further embodiment of an implantable device in accordance with the disclosure.

FIGS. 5A-5C illustrate a prosthesis mounted on the distal end of a delivery system, showing articulation of the delivery cable shaft.

FIG. 7-8 illustrates a portion of a delivery system in accordance with the disclosure without a prosthesis mounted thereon and with an outer portion of the system removed.

FIG. 8 is an illustration of an exemplary embodiments of a delivery system with a prosthesis mounted thereon.

DETAILED DESCRIPTION

Figure 1B:
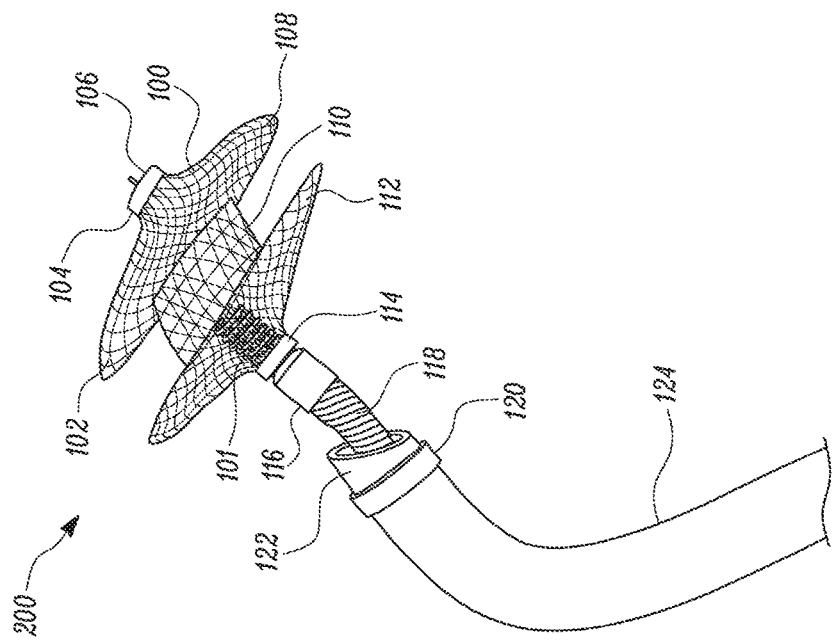

Reference will now be made in detail to the present preferred embodiments of the disclosure, examples of which are illustrated in the accompanying drawings. The method and corresponding steps of the disclosed embodiments will be described in conjunction with the detailed description of the system.

The exemplary embodiments illustrated herein can be used to more effectively close transvascular or transcameral access ports.

For purposes of illustration, and not limitation, as embodied herein and as illustrated in FIG. 1, a delivery system 200 is provided including prosthesis 100 mounted thereon. An illustration of a full exemplary system can be seen in each of FIG. 7 and FIG. 8, which are discussed in further detail below.

As referred to herein, the term "prosthesis" is intended to refer to a structural element that may or not be resorbable in whole or in part that can be used to replace a portion of anatomy and/or to close an opening in anatomy, particularly within the vasculature of the cardiovascular system. The prosthesis typically includes an adjustable framework or other body that can be used to close the openings in vasculature.

As illustrated, the distal region of the system 200 includes a distal end of an outer tubular member 124 that can be introduced through a lumen of a guiding catheter (not shown) that is used to deliver a prosthesis or perform some other function via a transvascular or transcameral access port. The distal end of the outer tubular member 124 is preferably provided with a distal radiopaque marker 120, such as one made at least in part from silver, gold, platinum or other radiopaque material, as desired. The distal tip 122 of the outer tubular member can be cut on a bevel and be provided with a marker that is aligned with the bevel near the beveled tip to facilitate guiding the device across the wall of the inferior vena cava into the aorta, for example. The bevel may be at any suitable angle, but is preferably offset from a central axis of the catheter by an angle between about 30 degrees and about sixty degrees, or any angular increment therebetween of about one degree. In an illustrative embodiment, the angle can be about 45 degrees. It has been found that such beveling of the tip helps to reduce "canting" or undesirable tilting of the implant during installation. The outer tubular member can be articulable or steerable at its distal end to facilitate maneuverability of the system. However, as discussed further below, the intermediate member 118 is preferably flexible, and can help eliminate the need for a steerable outer tubular member.

Outer tubular member 124 may be made from a variety of materials. For example, the sheath 120 can include a multi-layered co-extrusion, such as those described in U.S. Pat. No. 6,464,683 to Samuelson or U.S. Pat. No. 5,538,510 to Fontirroche. Each of the aforementioned patents is incorporated by reference herein in its entirety.

Any surface of various components of the catheters described herein or portions thereof can be provided with one or more suitable lubricious coatings to facilitate procedures by reduction of frictional forces. Such coatings can include, for example, hydrophobic materials such as Polytetrafluoroethylene ("PTFE") or silicone oil, or hydrophilic coatings such as Polyvinyl Pyrrolidone ("PVP"). Other coatings are also possible, including, echogenic materials, radiopaque materials and hydrogels, for example.

Within the outer tubular member 124 of the delivery system 200 a tubular delivery cable, or intermediate tubular member 118, is slidably disposed defining therethrough a central lumen along its length for slidably receiving a pushrod 180 therethrough, discussed in detail below. A distal region of the intermediate tubular member 118 can be configured to be of a lower stiffness, or durometer, than a proximal region of the cable to make it easier to articulate the distal end of the system, such as embodiments wherein the outer tubular member 124 have an articulable distal end or region. As illustrated, the intermediate tubular member 118 terminates in a coupling 116 for attachment to the prosthesis 100. The illustrated coupling 116 is a female member that receives a corresponding male coupling portion 114 on the prosthesis 100, but it will be appreciated that the coupling 116 on the delivery system can be male and that the coupling on the prosthesis can be female. In some implementations, a female coupling can be provided on the prosthesis that is defined by the inside of a coiled member, discussed in further detail below, that is received by a male threaded coupling on the delivery system. The coupling may be a threaded coupling but can also be a twist and lock coupling or the like.

Figure 1A:
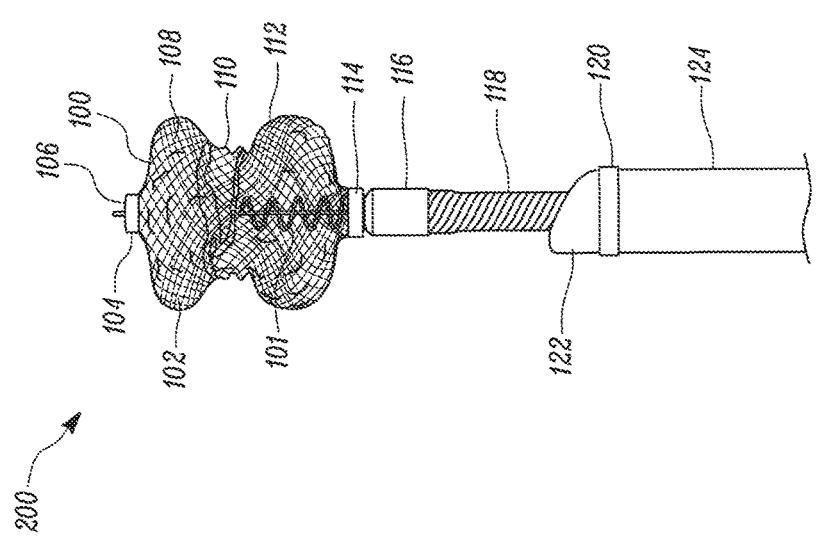

As further illustrated in FIGS. 1A-1B, a first exemplary embodiment of a prosthesis 100 is provided having a proximal end that connects to the delivery system, and a distal end 104 through which a guidewire can extend via a guidewire lumen 106. As illustrated, the prosthesis 100 includes an interior coil tension spring 101 that is configured to be contracted into a relaxed state when not being stretched. This results in the prosthesis being in a shortened, compressed state when relaxed. This is most evident in FIG. 1C, showing a compressed prosthesis 100 when the tension spring 101 is in a relaxed, unelongated condition. By stretching the coil spring, such as by pulling both ends of the prosthesis apart, the prosthesis takes on a more elongated profile with a smaller radial profile, such as depicted in FIG. 1A or 2C.

Figure 6C:
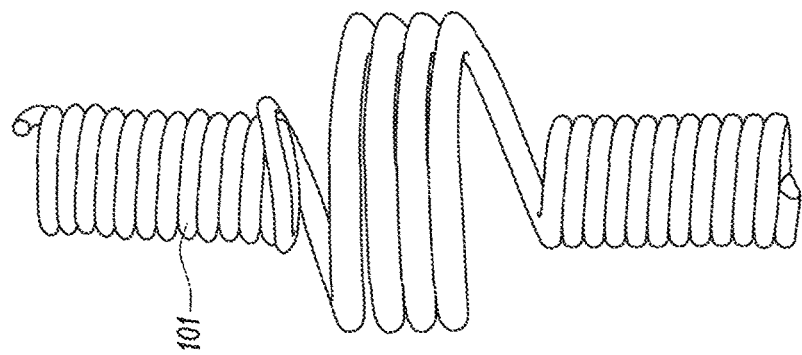
FIGS. 6A-6C illustrate variations of windings that can be used to help form the prosthesis.
Figure 6B:
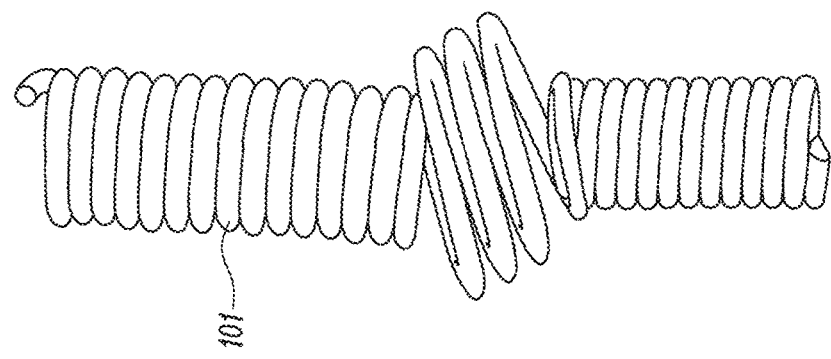
Figure 6A:
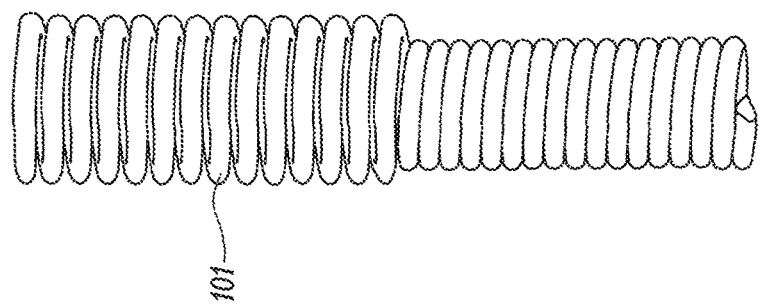

The coil spring 101 can have a substantially uniform outer and inner diameter along its length from a proximal end of the prosthesis to the distal end of the prosthesis. Alternatively, as illustrated in FIG. 6A, the coil spring 101 can have a first portion that has a larger diameter than a second portion, wherein the smaller diameter portion can be directed toward the proximal or distal end of the prosthesis. As illustrated in FIG. 6B, the coil spring can have three regions of different diameters, wherein a central region of the coil spring can have an enlarged diameter with respect to the diameter of either end portion. The end portions can be of the same or different diameters. Having an enlarged central portion can help prevent leakage after the prosthesis is installed as the coil can urge against the graft and/or mesh material within the adjustable neck 110 region of the deployed prosthesis between the lumens to cause the neck to bulge outwardly against the outer lumen walls to facilitate sealing and to help prevent leakage. The windings of the coil spring that is attached to the high pressure disc on the distal end of the prosthesis can be sized and shaped to prevent the hypotube from passing out of the distal end of the prosthesis, but to permit the guidewire to pass through. Similarly, the portion of the coil spring at the proximal end of the prosthesis that faces the delivery system can have a coil spring that is configured to be threaded onto a male end of the intermediate tubular member 118 to attach the prosthesis to the delivery system.

It will be appreciated that while a coil spring is primarily illustrated herein and is preferred, other resilient or elastic members can be used in place of the coil spring, or the prosthesis may instead be provided with retractable tethers (discussed in detail below with respect to FIG. 9 onward). For example, a single or a loop Elastic band that is attached to the radially expandable discs can be used, and/or any suitable material that can act as a tension spring and have a suitably low profile.

The prosthesis 100 further includes a mesh covering that may be braided from a variety of materials such as NiTi alloys or bioresorbable materials. It should be noted that, in some implementations, the prosthesis can be made from bioresorbable materials in its entirety. Suitable bioresorbable materials and techniques for construction can be found, for example, in U.S. patent application Ser. No. 11/398,363, filed Apr. 4, 2006, and U.S. patent application Ser. No. 14/461,159, filed Aug. 5, 2014, each of which is incorporated by reference herein in its entirety for any purpose whatsoever.

The mesh covering preferably defines at least one proximal lobe, or disc 112 and at least one distal lobe, or disc 102 joined by a narrowed neck 110 region that can be adjustable in radial dimension so as to permit a custom fit during implantation to minimize or eliminate leakage from the aorta and IVC. The mesh covering is joined at each of the proximal and distal ends to the respective proximal and distal ends of the coil spring. If desired, the disc 102 can be a high pressure endolumenal disc configured for placement against an inner arterial wall and disc 112 can be a low pressure disc configured for placement, for example, against an inner wall of the inferior vena cava.

The interior of the mesh can be filled with a woven graft material 108 and/or an elastomer with a coagulating coating, such as polyethylene glycol (PEG), or other non-thrombogenic, bio-inert polymer or polymer precursor.

For example, as illustrated in FIG. 1D, which presents a cross section of prosthesis 100, the distal face of the distal lobe or disc can include a first disc shape graft portion 108a that has a continuous surface except for a small hole or aperture 108b at the center thereof for surrounding the distal end of the coil spring 101 where it meets the mesh to permit the guidewire to pass through the distal end of the prosthesis. This first disc shaped portion 108a can be joined about its outer periphery (e.g., by weaving or stitching) to a second disc shaped portion 108c which also defines therein a central aperture 108d which may be slightly larger than 108b to permit passage therethrough of the coil spring which in turn is sized and shaped to permit passage therethrough of a pushrod (e.g., a stainless steel or NiTi hypotube, or polymeric (e.g., PEEK) or composite (e.g., carbon fiber) tubular member) of the delivery system containing the guidewire (discussed below). A further tubular graft portion 108e can be attached to and depend in a proximal direction from the proximal face of second disc shaped portion 108c to line the neck region of the prosthesis 100 and to surround the central region of the coil spring 101. If desired, portion 108e can be stitched at one or more locations to the mesh structure. In some implementations, the graft material 108 can still further include a third disc-shaped portion 108f attached to the proximal end of tubular portion 108e also defining a central aperture therein 108g for permitting passage of the coil 101. Disc 108f can similarly be joined about its periphery via weaving or stitching to a fourth, proximal disc 108h defining therein a central aperture 108i, which in turn surrounds the proximal end of the spring where it meets the proximal portion of the mesh to seal around the spring. The outer periphery of the four aforementioned discs may be stitched to each other and to the mesh to ensure proper registration of the mesh with the graft material.

As further illustrated in FIG. 1C, a pushrod 180 is slidably disposed within the lumen of the intermediate tubular member 118. The pushrod includes a proximal end attached to an articulable proximal handle (see e.g., FIGS. 7 and 8) and a distal end that abuts an inner surface of the distal end portion of the prosthesis 100. Specifically, the distal central opening of prosthesis 100 is large enough to permit a guidewire to pass therethrough, such as between 0.010 and 0.060 inches or other suitable diameter. Preferably, the aperture is small enough for the distal end of the pushrod 180, which defines a central lumen to slidably house the guidewire, to not pass through the opening, and instead urge against the inner distal surface of the prosthesis. Instead, the distal end of the pushrod (or push tube, as desired), abuts an inner distal surface of the prosthesis at or near the location of the opening. For example, the inner distal surface of the prosthesis can define a shoulder about the opening that the push rod pushes against, or if desired, the windings of spring 101 can be such that the most distal windings permit the guidewire to pass through, but not the push rod/push tube.

Figure 2A:
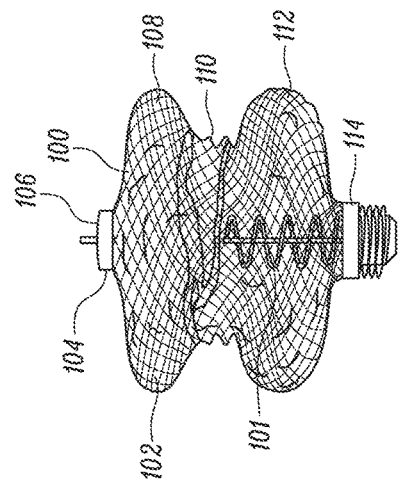
FIGS. 2A-2D illustrate various aspects of the prosthesis delivered by the device of FIG. 1.
Figure 2B:
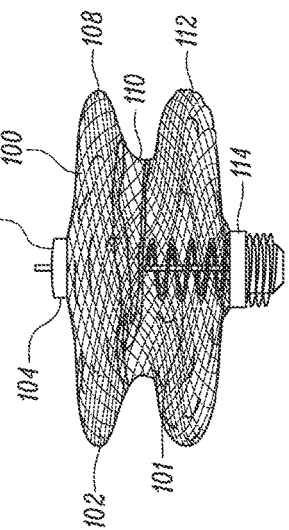
Figure 2C:
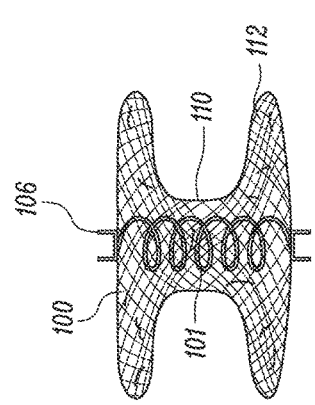
Figure 2D:
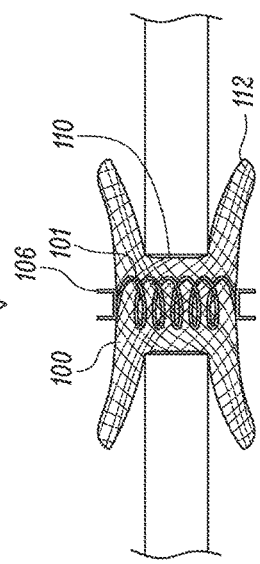

FIG. 2A is a schematic cross sectional representation of the prosthesis 100 in an extended or longitudinally stretched state wherein the coil spring 101 is in a stretched condition, and FIG. 2B illustrates the prosthesis in a relaxed condition in situ after installation gripping both sides of a lumenal passage. FIG. 2C similarly depicts an outer view of a prototype prosthesis 100 in an expanded condition wherein the push rod/push tube is urged distally within the delivery system (not shown) against the distal end of the prosthesis to cause the coil spring to stretch longitudinally. FIG. 2D illustrates the same prosthesis in a relaxed condition after the push rod/push tube is withdrawn. As can be appreciated, the coil spring 101 forces each of the lobes or discs including the exterior mesh with graft material inside to flatten and better contact the wall of the vessel (or chamber, depending on the application) and thereby better achieve hemostasis.

Figure 3C:
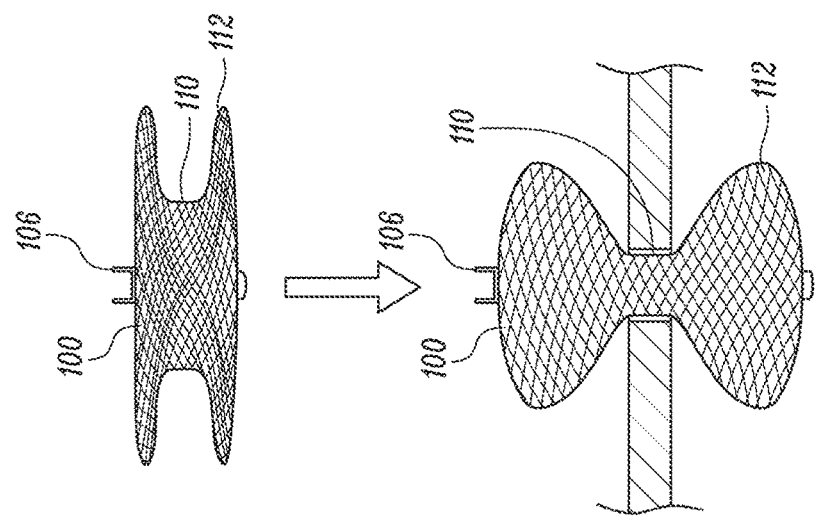
FIGS. 3B-3C illustrate examples of prior art prostheses.
Figure 3B:
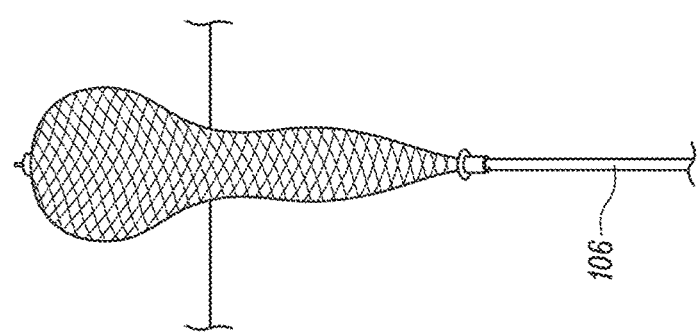
Figure 3A:
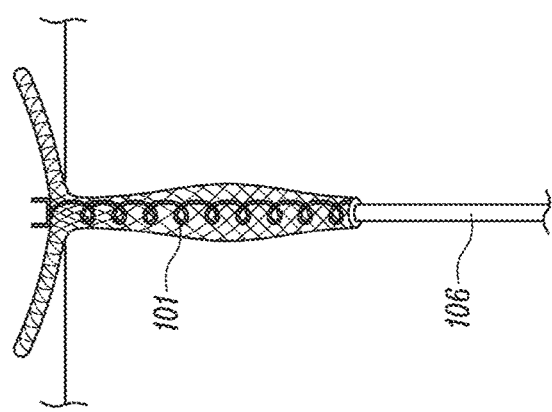
FIG. 3A illustrates an embodiment of a further prosthesis in accordance with the disclosure.

FIG. 3 illustrates relative performance between a disclosed embodiment and prior art embodiment. For example, an exemplary embodiment having a first disc section constructed as described above is presented in FIG. 3a. This embodiment resists pull-through the lumenal or chamber wall because the spring, or elastic member, is attached to the center of the distal or "high-pressure" disk (that could be located within an artery, for example), which causes the distal disk to flatten. Prior art embodiments (FIGS. 3B & 3C), such as Amplatzer Duct Occluder product, does not have such an elastic member or spring, and therefore assumes an oblong configuration during the retraction phase of deployment (arrow) and therefore is susceptible to inadvertent pull-through, which naturally leads to a potentially dangerous situation for the patient.

Figure 4C:
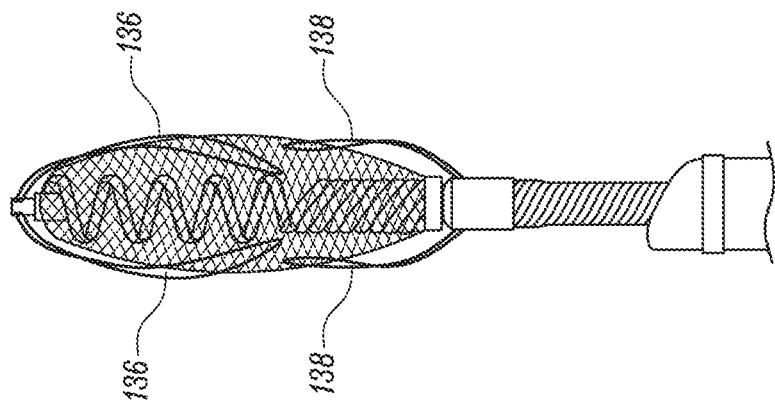
FIGS. 4A-4C illustrate a further embodiment of an implantable device in accordance with the disclosure mounted on the distal end of a delivery system.
Figure 4B:
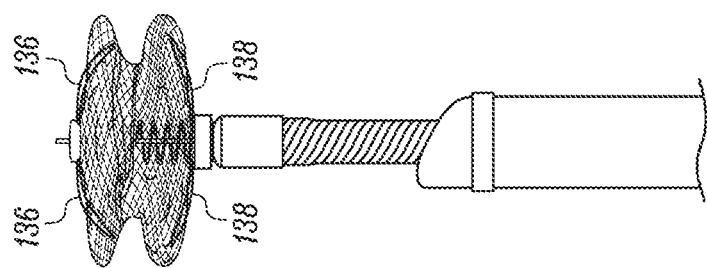
Figure 4A:
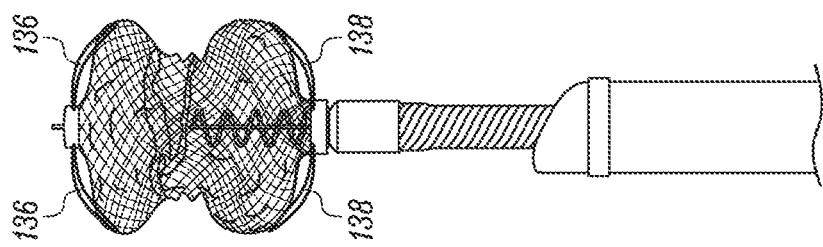

FIGS. 4A-4C illustrate a further embodiment of a prosthesis that, in addition to having all of the aforementioned structural features, additionally include additional elongate radially oriented struts or "wings" 136, 138 that are attached to the mesh of the prosthesis at the distal and proximal faces of the prosthesis, extending from a radially central portion of the prosthesis to an outer periphery of the prosthesis. These struts enhance the collapsibility of the prosthesis under the action of the spring or elastic member. While these wings or struts can be constructed as loops, they can be made in any desirable or suitable manner. FIG. 4A illustrates such a prosthesis in a longitudinally expanded configuration wherein the mesh envelope is stretched longitudinally over the graft material and spring, whereas FIG. 4B illustrates the prosthesis in a relaxed condition wherein it can seal against one or more lumenal walls. FIG. 4C further illustrates the prosthesis in a fully longitudinally expanded configuration wherein the push rod/push tube is fully extended causing the prosthesis to collapse radially inwardly so that it can be inserted into a delivery sheath. Significantly, this design permits the device to be retrieved and removed, or removed and repositioned and reimplanted and moved as desired. In other words, the combination of the elastic member or spring and delivery system with a push rod or push tube greatly enhances deliverability and placement of the prosthesis.

FIG. 4D illustrates an alternative embodiment of a prosthesis 140 that includes a main body formed from an inflatable, preferably bioresorbable material that is configured to seal a transcameral or transvascular access port, or other anatomical opening to be sealed. As illustrated, the prosthesis 140 has a proximal end attached to coupling 114 that in turn is removably attached to a coupling 116 located at the distal end of the intermediate tubular member 118. A lumen (not visible) passing through member 118 can carry fluid therethrough for inflating prosthesis 140 during delivery. Fluids, such as biodegradable polymer, resin or saline can be used to inflate prosthesis 140.

Fluid ports (not visible) can be provided in each of members 114, 116 to facilitate the inflation. Optionally, a guidewire port 106 can additionally be included. Wings 136, 138 can also be included to hold against the interior surfaces of the aorta and inferior vena cava, for example, while the inflatable body of the prosthesis 140 spans the gap between the two vessels and protrudes slightly into each vessel. The prosthesis 140 can be radially compressed within the distal end of outer tubular member 124 as with prosthesis 100. The compressed prosthesis 140 can be delivered to the site at which it is to be implanted, and the wings 136 can be deployed inside the aorta, for example, or other first location. The outer tubular member/sheath 124 can be retracted proximally thereby exposing the entire prosthesis 140 to the surrounding anatomy. A fluid actuator (e.g., fluid plunger that is actuated linearly or rotationally with a rotating handle driving screw) can then be depressed/actuated causing inflation fluid to be directed through the delivery system and into the prosthesis 140. The prosthesis 140 can be inflated to a desired extent to block leakage, and the wings 138 can be deployed (before, during or after inflation), causing the prosthesis to be lodged within the desired location. The wings/struts 136/138 could be wire loops that pass through the body of prosthesis, or can be mounted on either end of the prosthesis 140. Wings 136/138 are preferably shaped so they can be easily collapsed and retrieved into the delivery system.

If it is desired to move or remove the prosthesis 140, the fluid can be evacuated from the prosthesis by moving the fluid actuator in the opposing direction. The prosthesis can then be repositioned and implanted, or withdrawn into the distal end of outer tubular member 124, as desired. If desired, a push rod or push tube can be used to assist in retrievability of the prosthesis 100.

FIGS. 5A-5C further illustrate an embodiment of the prosthesis in a collapsed state on a delivery system in various articulated/steered positions allowing for adapting to the oblique angle of the device necessary for deployment and final release of the device.

FIG. 7 is an end to end illustration of a portion of an example of delivery system in accordance with the disclosure without the prosthesis mounted thereon and with the outer tubular member removed. As can be seen in FIGS. 7 and 8, the device itself, as well as the outer tubular member, intermediate tubular member, and push rod or push tube each have proximal end attached to a handle or control knob and a distal end. The intermediate tubular member as illustrated in FIG. 7 includes a relatively stiff proximal portion attached to a back end 150, and a transition segment 148 that is in turn attached to a distal flexible segment that terminates in coupling 116.

As illustrated in FIG. 8, the outer tubular member 124, or main delivery catheter, includes a back end 160 including a handle and steering knob configured to articulate the distal end of main delivery catheter/outer tubular member 124 that is attached to a proximal tubular region which in turn is connected to a distal tubular region terminating in beveled tip 122 that preferably also includes a marker that tracks the bevel to facilitate installation and reduce canting, or tilting, of the prosthesis during installation. The actuator 160 can take on a variety of forms, such as those depicted in U.S. Pat. No. 6,488,694 to Lau and U.S. Pat. No. 5,906,619 to Olson, the specifications of which are incorporated herein by reference in their entireties.

Before the system is introduced into the patient via a guiding catheter (not shown), the push rod 180 is fully distally extended to radially collapse the prosthesis, after which the intermediate tubular member can be withdrawn into the distal end of the main delivery catheter 124. The intermediate tubular member 118, or delivery cable shaft, thus preferably has variable stiffness along its length with a softer distal segment allowing for adapting to the oblique angle of the device necessary for deployment and final release of the device.

However, the present disclosure provides additional embodiments. For example, if desired, the prosthesis can be provided with more than two discs or lobes.

Figure 9A:
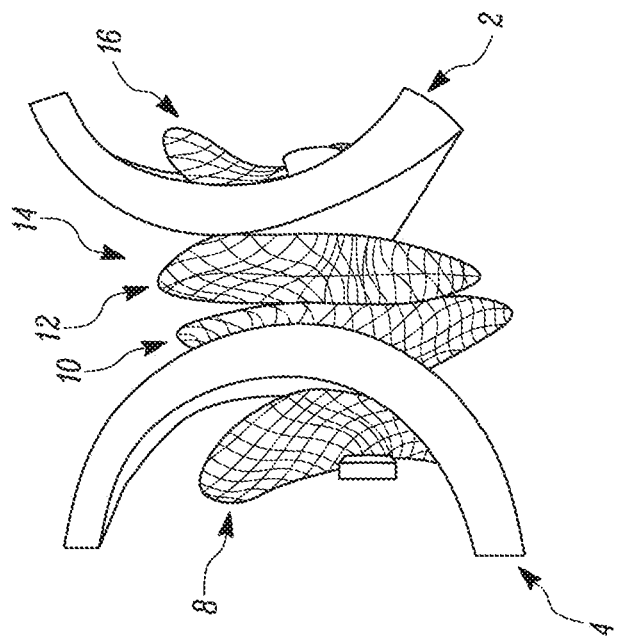
FIGS. 9A and 9B illustrate a further adjustable, compliant, maneuverable, retrievable and repositionable four disc/lobe closure system.
Figure 9B:
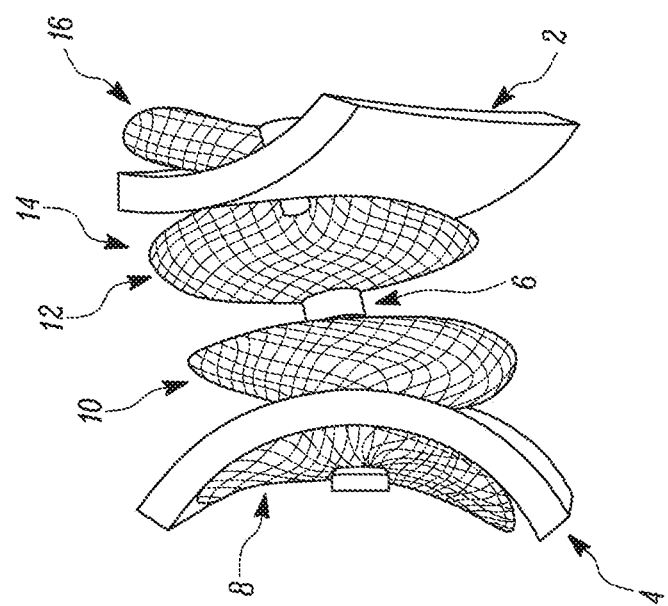

For purposes of illustration, and not limitation, FIGS. 9A and 9B illustrate a further adjustable, compliant, maneuverable, retrievable and repositionable four disc/lobe closure system that resembles the two lobe system discussed above, except that two additional discs or lobes are provided between the proximal and distal lobes. While the discs are depicted as being formed from a NiTi alloy, it will be appreciated that any suitable material can be used.

Figure 14A:
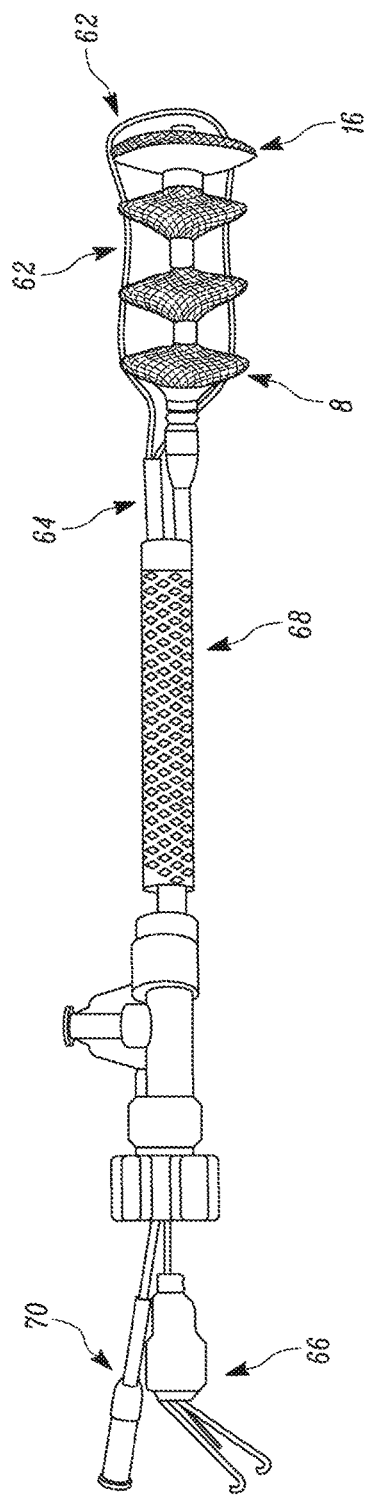
FIG. 14A-14B illustrate the prosthesis and delivery catheter with tethers running through all four and three prosthesis and into a guiding sheath of the delivery catheter.
Figure 14B:
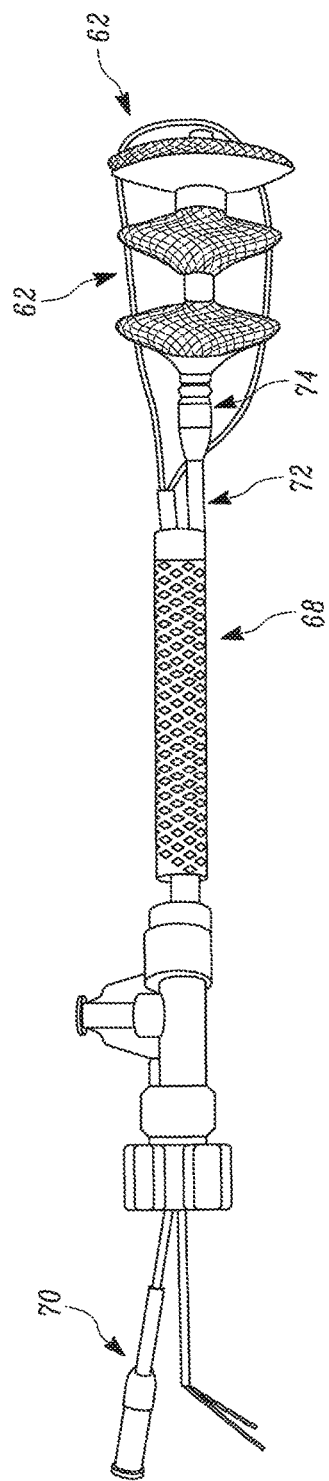
Figure 16B:
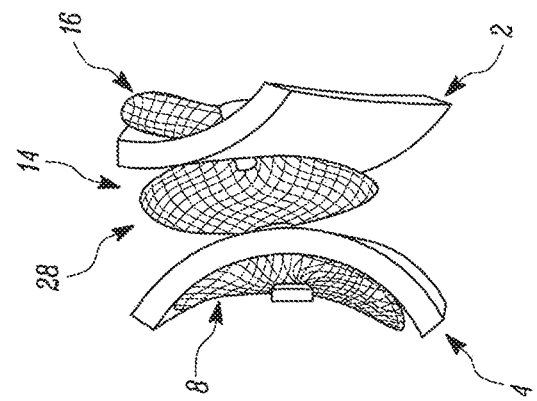
Figure 16A:
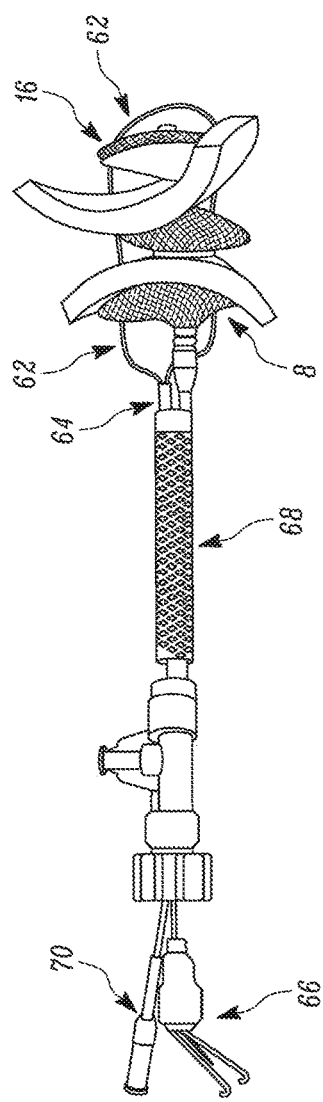

As illustrated in FIGS. 9A and 9B, in an installed formation, the prosthesis includes a first high pressure or artery facing disc 16 that is deployed in the aorta, for example. The caval wall 4 and arterial wall 2 are presented with the prosthesis mounted therein. A next proximal disc 12 is provided for deployment against the outer wall of the aorta. A marker band 6 is also provided to enhance retention of the prosthesis. A third external caval disc 10 is provided for urging against the exterior of the inferior vena cava, and a fourth disc 8 is provided to seat within the IVC. One or more of the four discs can be provided with an exterior curvature or taper 14 that facilitates sealing, and all four discs can be formed from a mesh as with embodiment 100. A spring need not be located within the prosthesis of FIG. 9, but it can be. Collapsing of the prosthesis can be facilitated with tethers 62 that run through all four and three prosthesis and into a guiding sheath 64 of the delivery catheter as illustrated in FIG. 14A-B. As illustrated in FIGS. 16A-B, the tethers can be withdrawn and pulled and the delivery catheter can be held fast to tighten the tethers until all leaks are stopped. The tethers can then be tied off or clipped, and the delivery system can be removed accordingly.

Figure 10B:
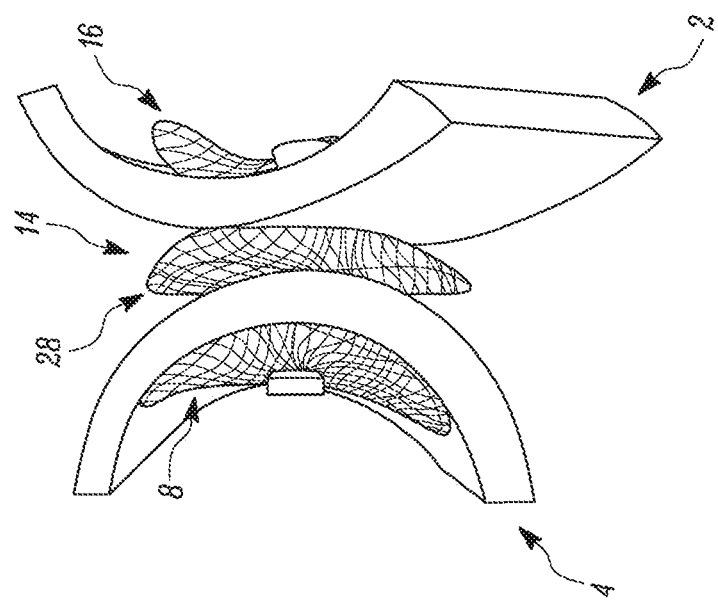
FIGS. 10A-10B illustrate a three disc/lobe embodiment wherein a central disc is located between the aorta and inferior vena cava.
Figure 10A:
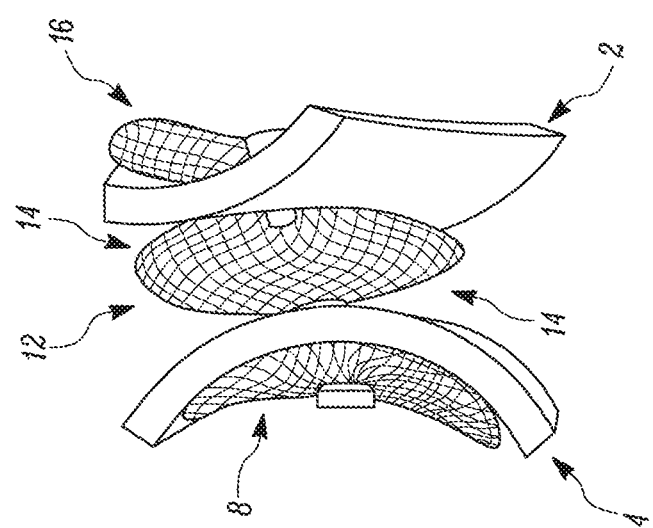

FIG. 9A shows the prosthesis after deployment but before the tethers are cinched, while FIG. 9B shows the tethers after cinching. FIGS. 10A-B similarly show a three disc/lobe embodiment wherein a central disc 28 is located between the aorta and inferior vena cava. The construction is otherwise the same as the embodiment of FIG. 9, and may be constructed with an interior spring if desired as with embodiment 100 if desired, and/or can be provided with tethers as the embodiment of FIGS. 9A-9B. The embodiment of FIGS. 10A-B may also be provided with a guidewire lumen 30.

Figure 11B:
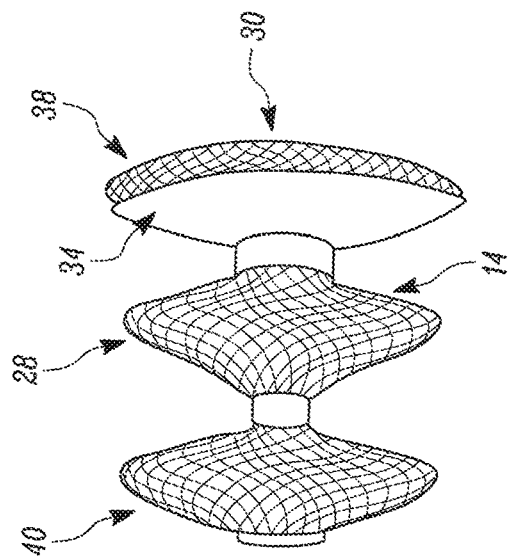
FIG. 11A-11B illustrate a four disc and three disc embodiment of a prosthesis.
Figure 11A:
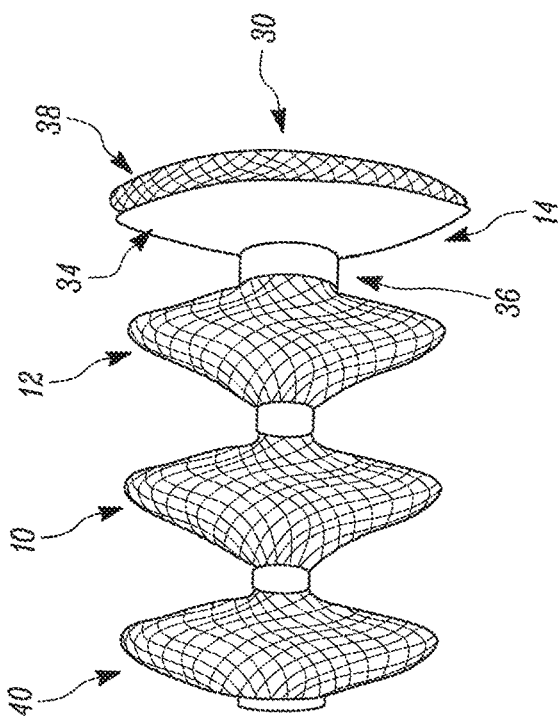
Figure 12B:
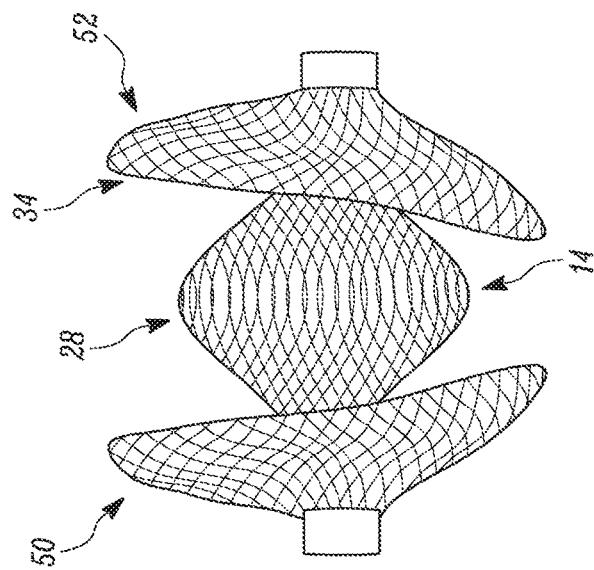
FIG. 12A-12B illustrate the prosthesis in a deployed condition with the end disc flattened.
Figure 12A:
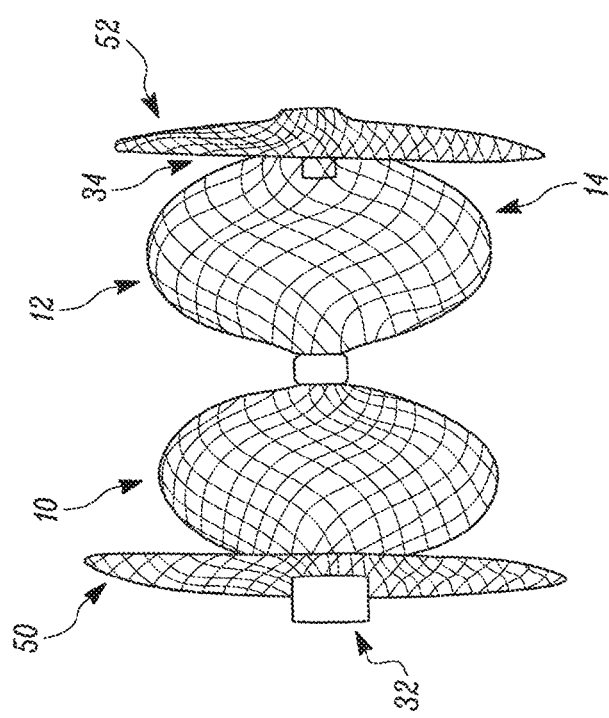

FIG. 11A depicts a four disc embodiment of a prosthesis wherein a radiopaque and/or elastomer covered neck 36 is provided between the high pressure disc 38 and the second disc 12, wherein the elastomer 34 is designed to help prevent leakage. Also visible are the low pressure caval disc 40 and third disc 10, wherein discs 10, 12 and 40 each have radiopaque markers disposed therebetween. FIG. 12A shows the prosthesis in a deployed position wherein the end discs are flattened and the middle discs are not fully flattened. FIG. 11B similarly provides a three disc version wherein like reference numbers indicate like structures.

Figure 13B:
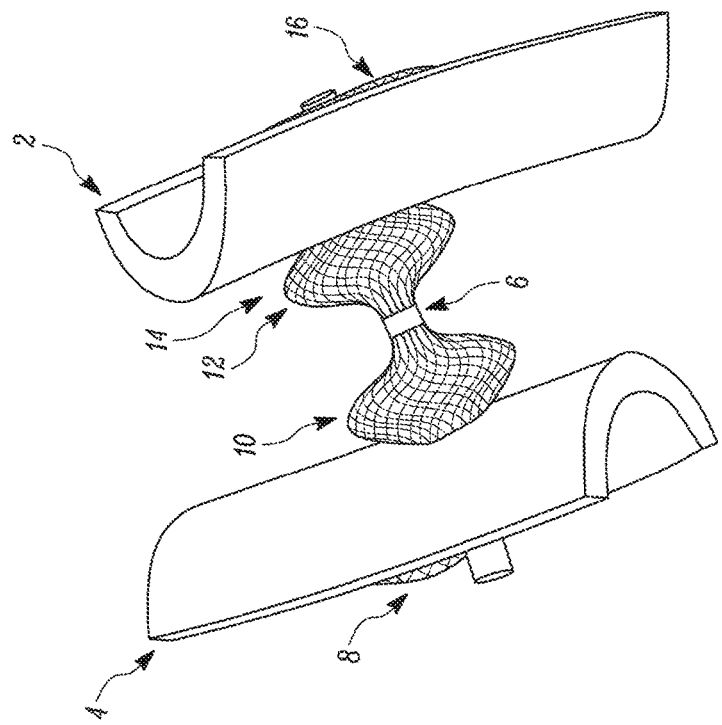
FIG. 13A-13B illustrate the prosthesis in a deployed condition with the end disc flattened.
Figure 13A:
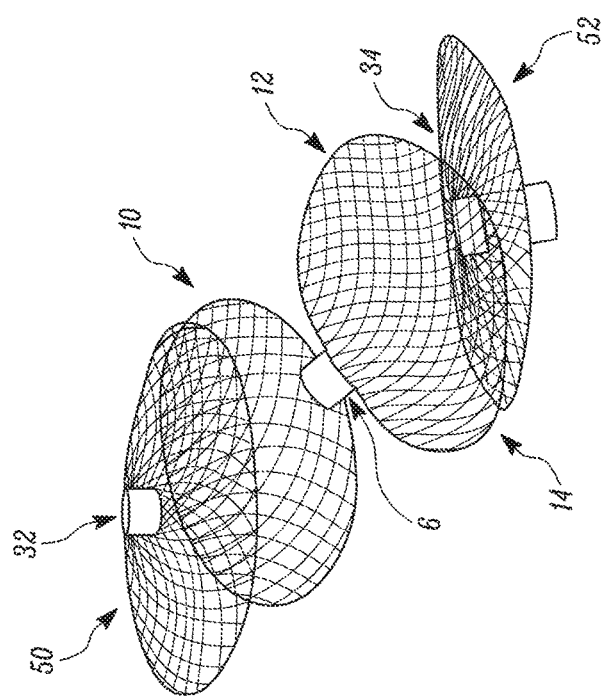

FIG. 12A illustrates a four disc embodiment in a deployed condition wherein the caval disc 50 and aortic disc 52 are compressed and fixed, and the intermediate discs 10, 12 are expanded to express a taper 14 to facilitate sealing and prevent leakage. FIG. 12B illustrates a three lobed prosthesis wherein the caval 52 and aortic 50 discs are fully deployed and flattened, and further wherein the central disc 28 is deployed to define a tapered sealing surface 14. FIGS. 13A-B show a further variant of a four disc embodiment in a semi deployed condition and in a simulated installed condition in anatomy.

Figure 15B:
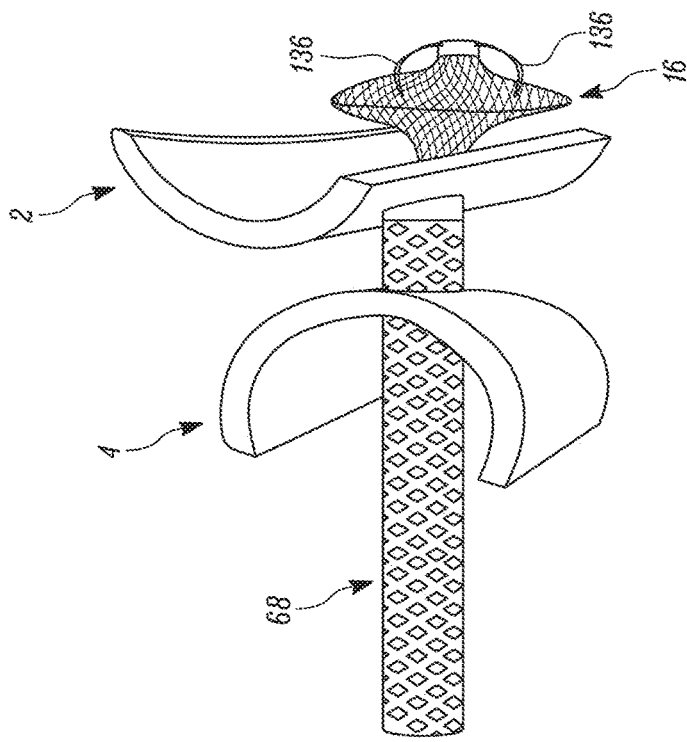
FIGS. 15A-15B and FIGS. 16A-16B illustrate a complete deployment of a three disc embodiment from beginning to end.
Figure 15A:
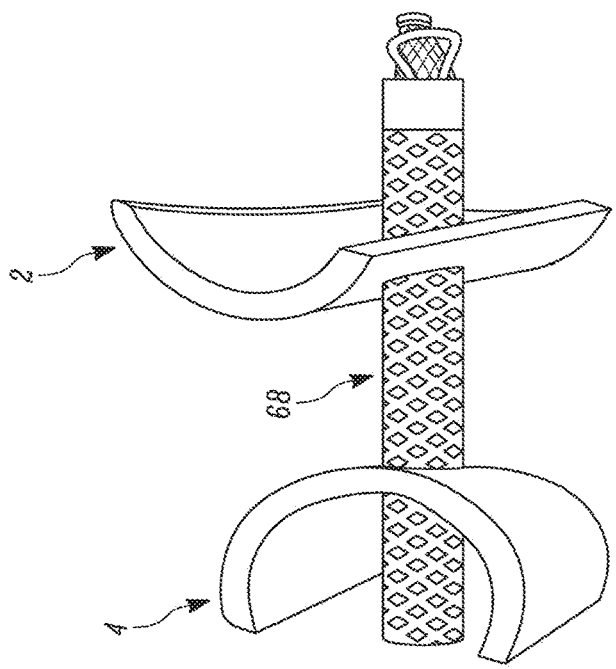

FIGS. 14A-14B illustrate four and three disc prosthesis embodiments respectively with tethers 62 routed through them, wherein the aortic disc 16 is located at a distal end of the assembly, and a most proximate disc 8 is also provided. The tethers 62 are directed through the prosthesis, and then proximally through a tubular member, or tether lumen 64, toward the proximal end of the delivery system 68 through a port and/or handle 66. A handle 70 is further provided that is attached to an elongated member or closure holding shaft 72 (e.g., tube or rod) that is attached to the prosthesis via a removable coupling, such as a holding, releasing and/or retrieval articulating screw with wire lumen. FIGS. 15-16 show a complete deployment of a three disc embodiment from beginning to end.

Figure 17A:
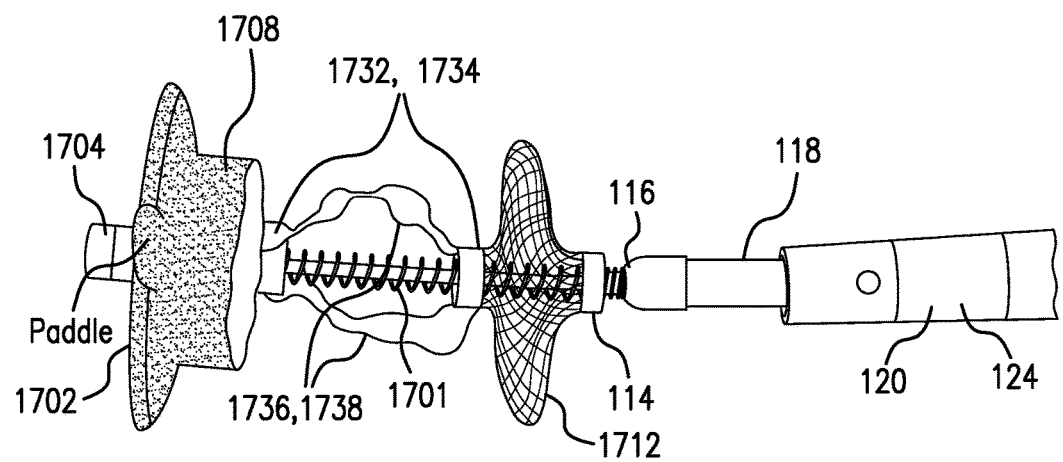
FIGS. 17-22 present a further illustrative embodiment of a telescopic closure prosthesis in accordance with the disclosure and method of use thereof.
Figure 17B:
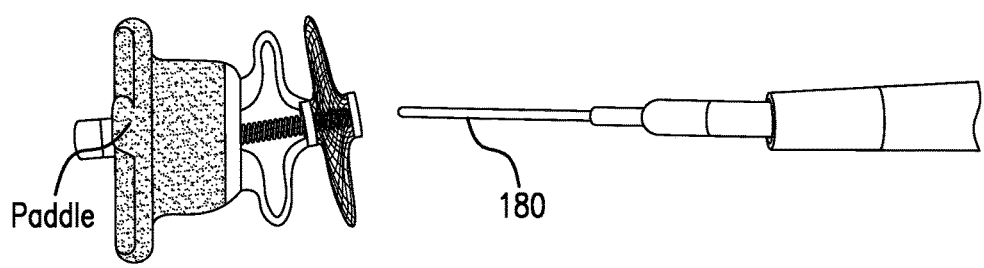
Figure 17C:
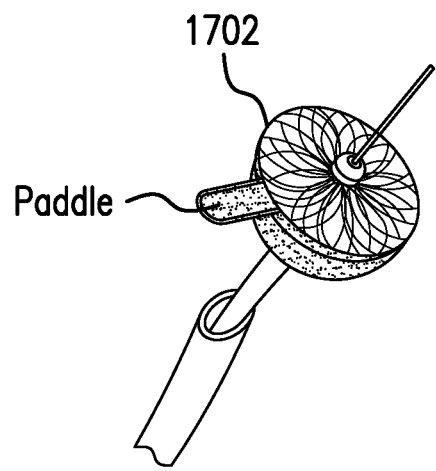
Figure 17D:
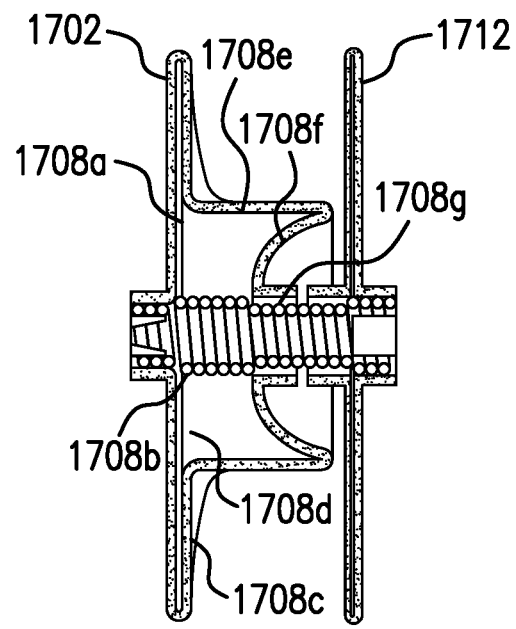
Figure 17E:
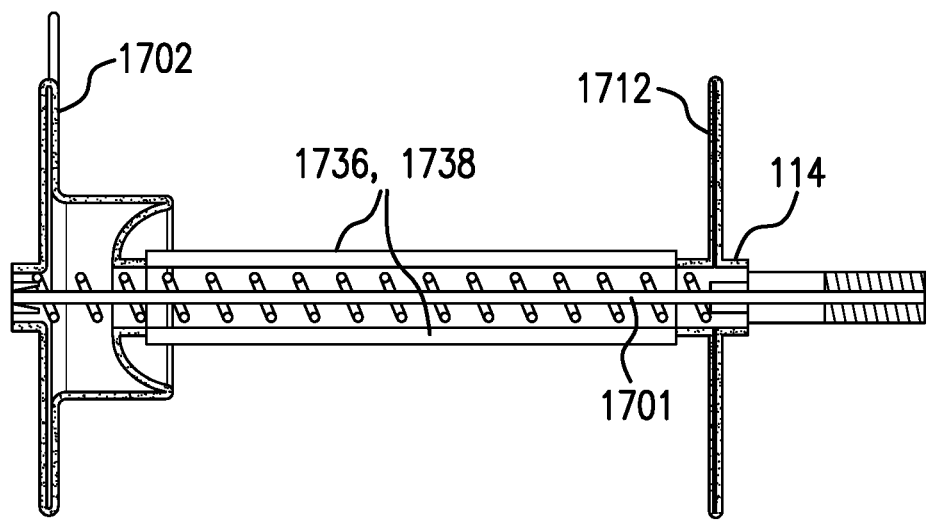
Figure 17F:
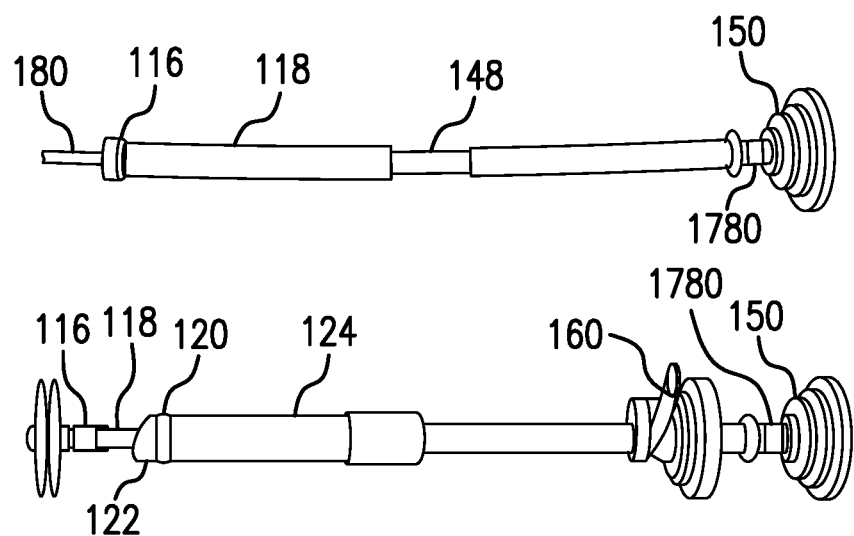
Figure 18:
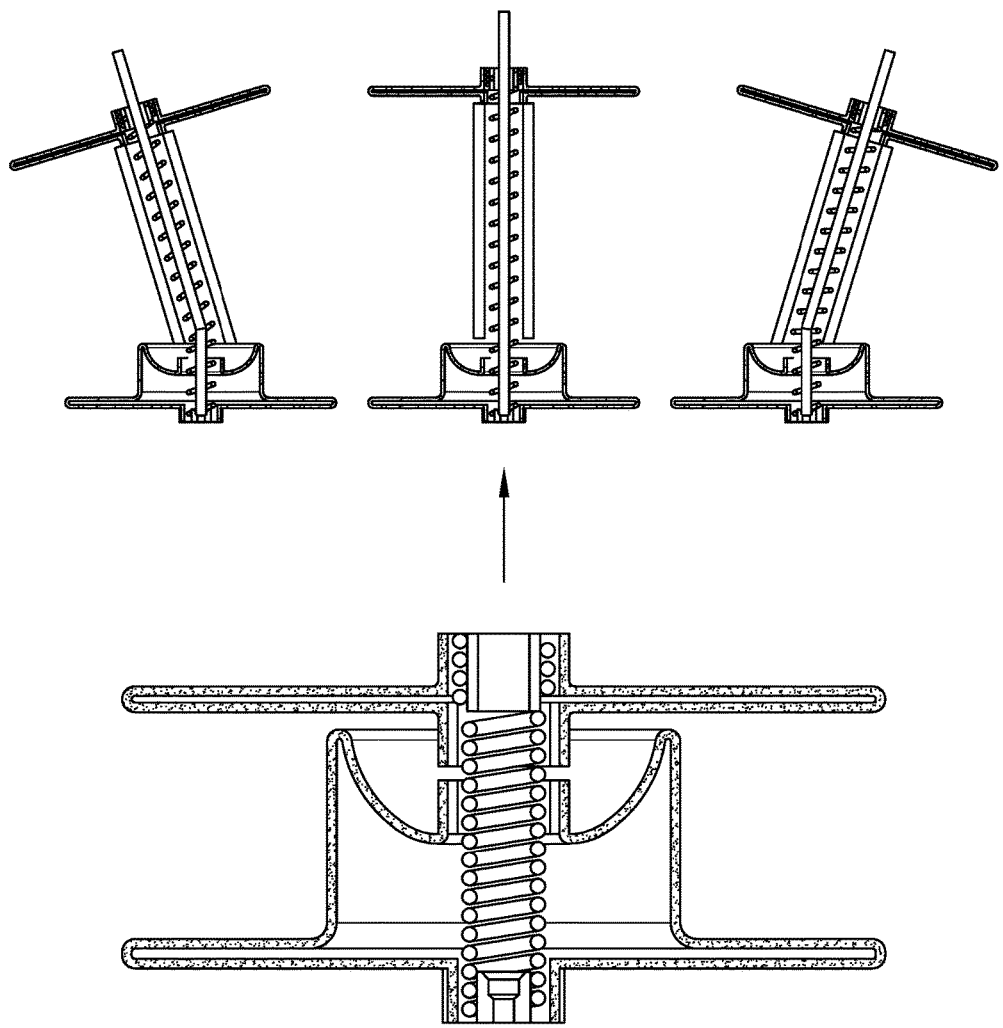

FIGS. 17-19 present a further illustrative embodiment of a telescopic closure prosthesis in accordance with the disclosure. The prosthesis can be delivered using the delivery catheter described herein above.

FIGS. 17A-17E illustrate particular structural aspects of the prosthesis 1700. As illustrated, prosthesis 1700 includes a distal disc 1702 and a proximal disc 1712 as with preceding prostheses described herein, connected by a tension coil spring 1701. However, prosthesis 1700 differs quite significantly in structure from any of the foregoing prostheses described herein. In pertinent part, although the discs 1702, 1712 are formed of a braided material, they are not connected by braided material, but are instead connected by the spring 1701, as well as the illustrated expansion limiting tethers 1736, 1738. Prosthesis 1700 is presented in a compacted form, as illustrated in FIG. 17D wherein the tension spring 1701 has fully collapsed the device axially. FIG. 17E, in contrast, illustrates the prosthesis 1700 in an axially expanded format.

Disc 1702 is also provided with a further structure, or "paddle" that extends radially outwardly from the disc 1702 when deployed. The paddle can be attached to the structure of the inner face of disc 1702 such that its orientation is parallel to a longitudinal axis of the delivery system when the prosthesis 1700 is collapsed. Since the paddle is attached to the planar inner face of disc 1702, it then reorients to being generally transverse, or even perpendicular, to the longitudinal axis of the delivery system when deployed. If desired, the paddle can be attached to any face of the prosthesis 1700, depending on how it is being delivered. Moreover, multiple paddles can be provided attached to the same or different discs. In one embodiment, two paddles are attached to the proximal face of the distal disc rather than one as illustrated that are positioned at the same general circumferential location of the disc (next to each other) or spaced apart from each other, such as by 180 degrees. In another embodiment, three or more (e.g., four five) paddles are provided that may be spaced from each other circumferentially uniformly or non-uniformly.

The paddle can be a wire frame as depicted and may be partially or completely covered by synthetic or living tissue or graft material, or may be uncovered. In the illustrated embodiment, a polyethylene terephthalate ("PET") fabric is used. Generally, with respect to prosthesis, fabric provided within the mesh discs (e.g., 1702) is made from a polyester with a non-stretchable weave, such as a braided polyester material. The material serves to reduce or prevent the flow of blood across the disc 1702. The fabric is preferably between about 0.003 to about 0.004 inches thick, and more generally can range from about 0.0005 to about 0.010 inches thick, or any increment therebetween of 0.0001 inches, as desired.

The outer fabric that resides over the neck region of the prosthesis 1700, for example, is preferably a knitted polyester and has conformability to the shape of the disc. Although this material is knitted and defines pores therein, it facilitates hemostasis, preferably immediate hemostasis, when disc 1702 is deployed. The material is also suitably configured to facilitate tissue ingrowth after implantation of the prosthesis. The outer fabric is preferably about 0.009 inches thick, and more generally can range from about 0.002 to about 0.010 inches thick, or any increment therebetween of 0.001 inches, as desired.

In use, the paddle provides pullout resistance when the prosthesis is deployed. Specifically, during delivery of the prosthesis, significant force is exerted by the prosthesis against the inner arterial wall above the opening through which the prosthesis extends. The paddle extends upwardly above the opening in the artery parallel to the direction of the artery. When the prosthesis is pulled on by the delivery system, the paddle is urged against the arterial wall above the hall, and prevents the prosthesis from being pulled out of the artery.

As can be appreciated from the figures, distal disc 1702 is configured for placement in an arterial environment, wherein graft material is disposed in the disc in a manner similar to the embodiment of FIG. 1C herein. Specifically, the distal face of the distal disc 1702 can include a first disc shape graft portion 1708*a* that has a continuous surface except for a small hole or aperture 1708*b* at the center thereof for surrounding the distal end of the coil spring 1701 where it meets the mesh to permit a guidewire to pass through the distal end of the prosthesis. This first disc shaped portion 1708*a* can be joined about its outer periphery (e.g., by weaving or stitching) to a second disc shaped portion 1708*c* which also defines therein a central aperture 1708*d* which may be slightly larger than 1708*b* to permit passage therethrough of the coil spring 1701 which in turn is sized and shaped to permit passage therethrough of a pushrod (e.g., a stainless steel or NiTi hypotube, or polymeric (e.g., PEEK) or composite (e.g., carbon fiber) tubular member) of the delivery system containing the guidewire, as with the embodiment of FIG. 1. A further tubular graft portion 1708*e* can be attached to and depend in a proximal direction from the proximal face of second disc shaped portion 1708*c* to line a neck region of the distal disc 1702 and to surround a portion of the coil spring 1701. In contrast to the embodiment of FIG. 1, distal disc 1702 of prosthesis 1700 further includes a concave graft portion 1708*f* defining an aperture 1708*g* in a center thereof to accommodate the coil spring 1701, as well as a distal floating sleeve or marker band 1732 that is configured to slide over an outer surface of the coil spring 1701 when the spring expands, whereas the distal face of disc 1702 is attached at its central region to the coil spring 1701.

The graft portions 1708*a*, 1708*c*, 1708*e*, 1708*f* cooperate with the exterior surface of the spring 1701 to define an interior compartment 1709 that can be used for a variety of purposes. For example, compartment 1709 can be used to include a beneficial agent, such as a coagulating gel, or other beneficial agent such as a pharmaceutical compound or other material. The concavity defined on the distal disc 1702 permits the sleeve 1734 of the proximal disc to be nested within the mesh of the distal disc, thus permitting a very compact configuration if needed. Instead of or in addition to a woven graft material, an elastic polymer and/or a hydrophilic polymer layer can be sued to enhance closure and placement of prosthesis 1700, especially in a calcified fistula.

Proximal disc 1712 is similar in many respects to disc 112 of the embodiment of FIG. 1, except that it is not attached to the distal disc 1712 at its distal end, and is instead attached to a proximal floating sleeve or marker band 1734 that is configured to slide over an outer surface of spring 1701, as with distal floating sleeve or marker band 1732. Discs 1702, 1712 are illustrated as being connected at sleeve/marker bands 1734, 1732 by way of expansion limiter tethers 1736, 1738. The net result is that when the prosthesis 1700 is expanded axially as illustrated in FIGS. 17A, 17E, the discs 1702, 1712 maintain a relaxed condition as when deployed fully until the expansion limiter tethers 1736, 1738 begin to be placed under tension. When expansion limiter tethers 1736, 1738 are placed under tension, the discs 1702, 1712 will deform by decreasing in radial dimension, which can be useful when loading the prosthesis 1700 into a delivery sheath as described herein, or if it is desired to remove the prosthesis and reposition it in situ during the procedure. Expansion limiter tethers 1736, 1738 further act to prevent the coil spring 1701 from being overly stretched or yielded (e.g., deformed plastically), and can also act to hold the prosthesis 1700 together in the event that spring 1701 fractures.

Prosthesis 1700 provided additional advantages as compared to the other prostheses described above. By virtue of the inner ends of the discs 1702 and 1712 being able to freely slide over the coil tension spring 1701 independently of each other, it is possible to have a truly telescoping prosthesis. This permits the discs 1702, 1712 to be in an optimal configuration when installed, yet allow for different distances between the discs 1702, 1712, thus permitting a prosthesis 1700 of the same design to be used in multiple patients having larger or smaller distances between adjacent lumens that incorporate the prosthesis 1700. Further, the discs 1702, 1712 of prosthesis 1700 can be made in whole or in part from bioresorbable material metallic or polymeric materials.

In addition to providing true telescoping ability, decoupling the discs 1702, 1712 from each other greatly facilitates articulation of the prosthesis. As seen in FIG. 18, the distal disc 1702 can easily be articulated with respect to the proximal disc 1712, by an angle that is almost 90 degrees (e.g., 60, 70, 80 degrees). If desired, a backend push rod extension limiter 1780, such as in the form of a bushing over the shaft of the delivery catheter (FIG. 17F) can be provided to avoid overly stretching the prosthesis axially.

Figure 19A:
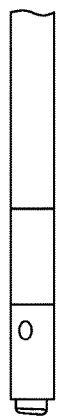
Figure 19B:
Figure 19C:
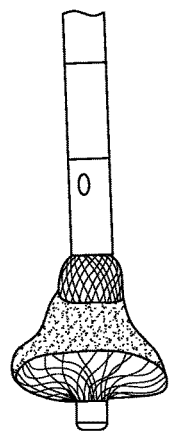
Figure 19D:
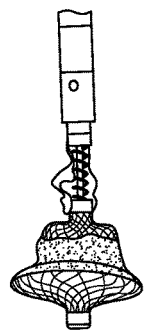
Figure 19E:
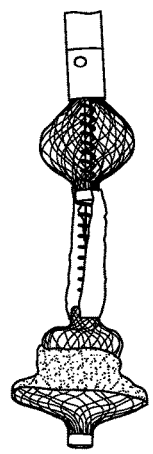
Figure 19F:
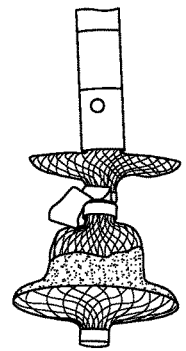
Figure 19G:
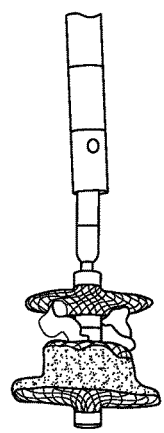
Figure 19H:
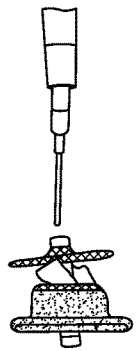

The delivery system can be used to collapse discs for loading, full retrieval even after full deployment and individual control of discs. For example, as illustrated in FIG. 19A, an implant is loaded within the delivery system and delivered to a target site for deployment. The distal disc 1702 is then advanced from the catheter into an artery, for example, as illustrated in FIG. 19B. FIG. 19C illustrates the distal aortic disc 1702 fully deployed, and preparing it to be seated. FIG. 19D illustrates axial extension of spring 1701, by pushing on pushrod 180. The proximal venous disc 1712 is then deployed as shown in FIG. 19E. FIG. 19F illustrates the proximal venous disc 1712 in a fully deployed condition to be seated. FIG. 19G illustrates releasing the prosthesis 1700 from the delivery system, which can then be removed, as illustrated in FIG. 19H. It will be appreciated that the prosthesis of FIG. 19 is not illustrated as having the paddle shown in other figures, but a paddle can be provided on the prosthesis if desired.

FIG. 20 illustrates further aspects of the prosthesis and delivery system, showing the advantages of using the paddle described above that is attached to disc 1702. The prosthesis is illustrated in FIG. 20A in a deployed condition resting on the delivery system with a guidewire passing through the central lumen of the system and out of the distal end. FIG. 20B illustrates the paddle framework independently of the prosthesis. As illustrated, the framework can simply be a loop of metallic or other suitable material that is then attached to the framework of the prosthesis 1700. Markers can be provided along a portion or the entirety of the paddle structure, or the paddle structure can be formed of radiopaque material, for example, such as 70% NiTi and 30% platinum wire, known as "DFT" wire.

Figure 20A:
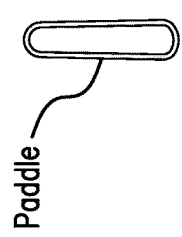
Figure 20B:
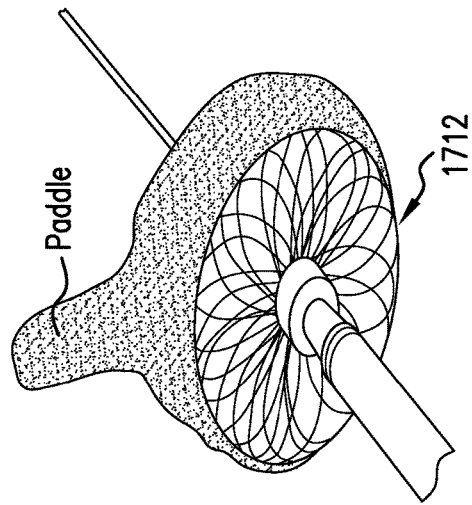
Figure 20C:
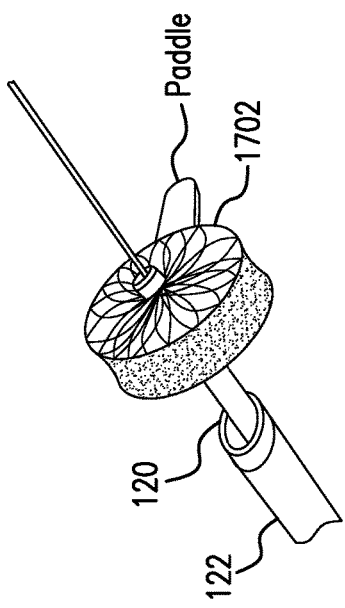
Figure 20D:
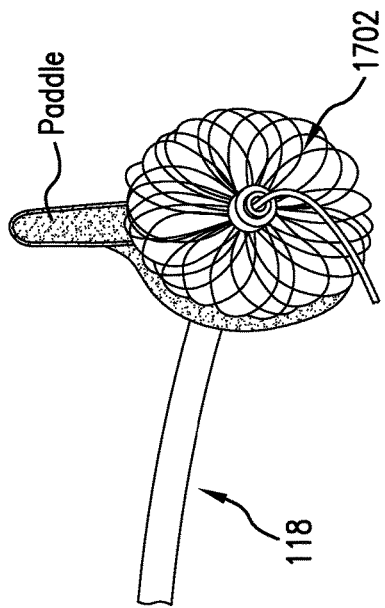

FIG. 20C illustrates prosthesis 1700 in a collapsed condition with the paddle attached to the disc 1702, and further wherein the paddle includes graft material attached thereto. FIG. 20D illustrates a proximal-distal view of prosthesis mounted on the delivery system, illustrating the proximal face of the proximal disc. FIG. 20E is a side view of the expanded prosthesis illustrating the positioning of the paddle attached to the distal disc. FIGS. 20F and 20G further illustrate side views of the prosthesis 1700 particularly illustrating the placement of graft material on the inner face of each of the proximal and distal discs and between the discs such that the graft material forms a "saddle" shape that presents as a concave projection when viewed from the side that has a minimum diameter near the middle of the neck region of the prosthesis 1700 that gradually widens toward each disc. This shape of the graft material as supported by the underlying structure of the prosthesis is believed to be advantageous in providing an effective seal after implantation, especially with respect to the arterial wall, such as the abdominal aorta. In some embodiments, the prosthesis 1700 is configured so as to not provide a complete seal with respect to the proximal disc that urges against the inner wall of the inferior vena cava (IVC), for example. In certain instances, complete sealing of the IVC of the implant may not be desired. This can be the case where it is desired for the vein to intake blood that is leaked from the corresponding artery that is being sealed by the distal disc. In practice, since the vein may not have significant positive pressure, the need for sealing may be negligible, and it may be advantageous, in fact, to maintain some degree of fluid communication between the vein and the space between the vessels via the hole in the vein as a part of the procedure.

Figure 20H:
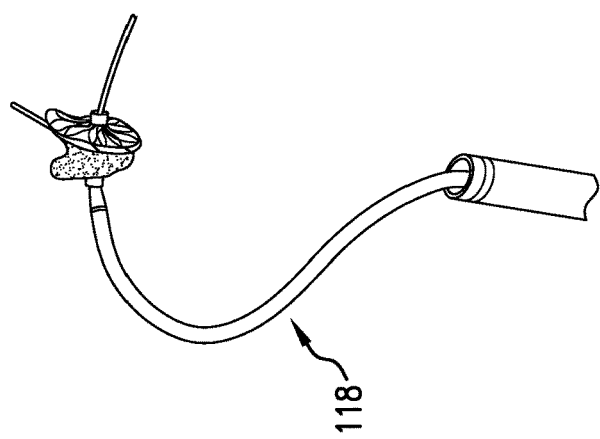
Figure 20G:
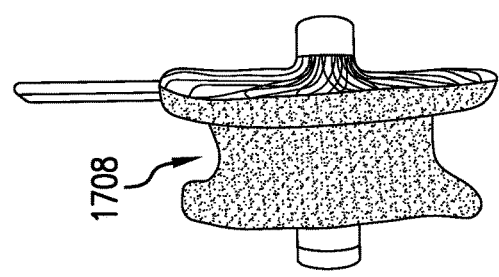
Figure 20F:
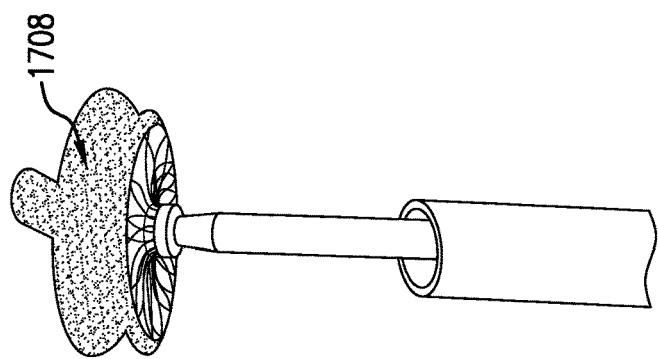
Figure 20E:
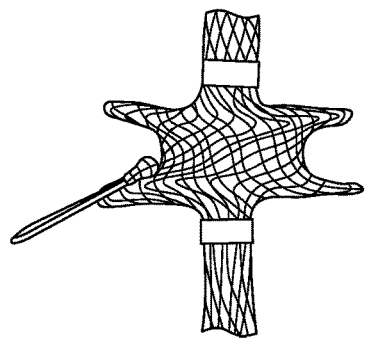

FIG. 20H illustrates positioning of the delivery system that can be effected by virtue of the flexible distal portion of intermediate tubular member 118. The flexibility of distal portion of intermediate tubular member 118 can be extremely advantageous as its flexibility permits it to be deformed into a geometry that permits it to effectively bend about 90 degrees with respect to a central axis of a proximal portion of the delivery system, as illustrated in FIG. 20H. Specifically, when implanting the prosthesis 1700 on the arterial side, the paddle is urged against the upper (i.e., cranial) wall above the hole in the artery (e.g., the abdominal aorta) to prevent the prosthesis 1700 from being pulled through the hole. However, during this alignment step, the paddle urging on the upper, inner wall of the artery can advantageously be used as a fulcrum, or "pivot point" to rotate the prosthesis into alignment horizontally such that the lower portion of the distal disc is also pulled against the inner wall of the artery, below the access hole through which the prosthesis 1700 extends. This movement about the "fulcrum" is effectuated by exposing the distal, flexible portion of intermediate tubular member 118 and pushing the delivery system distally into the vein (e.g., IVC) so that a bowing of the intermediate tubular member 118 occurs to obtain a serpentine configuration that resembles the shape of a reversed question mark ("?"), as illustrated in FIG. 20 by virtue of the prosthesis 1700 being constrained due to partial implantation. This maneuvering pulls the proximal face of the distal disc flush against the arterial wall, completing the implantation of the distal disc, and thus minimizing arterial leakage. It can be particularly advantageous to provide a marker at the base of the paddle where the paddle meets the prosthesis distal disc, because such a marker, when so positioned, is very useful for indicating the location of the arterial hole under fluoroscopy because the marker is thus located at the "fulcrum" or pivot point, discussed above. Including a fabric on the paddle can provide additional resistance to pullout of the prosthesis during implantation as the inner surface of the arterial wall can be rough due to plaque formation. The fabric of the paddle can urge against and somewhat adhere to this uneven surface, facilitating implantation of prosthesis 1700.

Figure 21E:
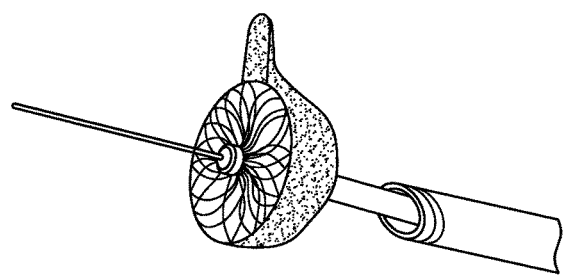
Figure 21D:
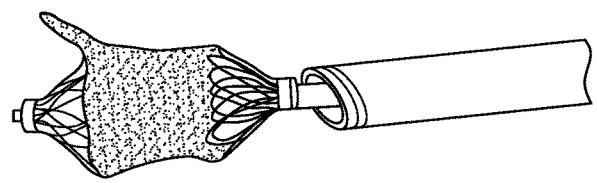
Figure 21C:
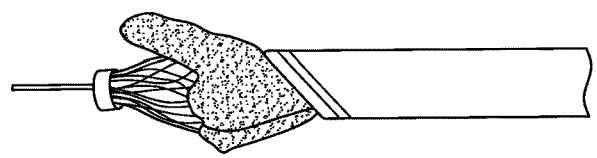
Figure 21B:
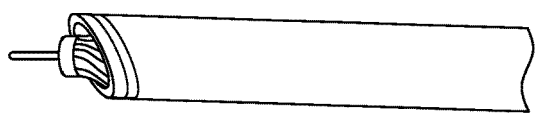
Figure 21A:
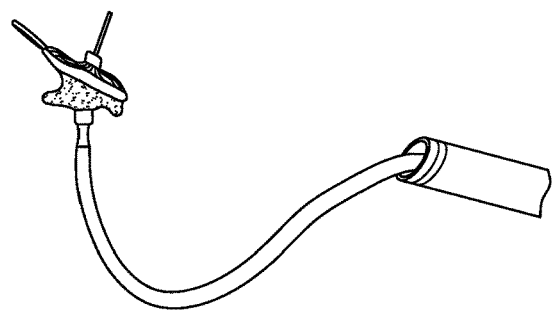

FIGS. 21A-E illustrate various stages of deployment of the prosthesis with respect to the delivery system. FIG. 21A illustrates the prosthesis 1700 in a deployed condition with the paddle extending radially outwardly with respect to the prosthesis. As illustrated, the distal tip 122 of the outer tubular member can be cut on a bevel to facilitate guiding the device across the wall of the inferior vena cava into the aorta, for example. It is also advantageous to provide a marker band, as illustrated, that is also in an angle at the beveled end of the distal tip 122. Such a marker band is very helpful in alignment of the device in use, but it also informs the user when the distal tip 122 is traversing the walls of the artery and vein as it is being withdrawn proximally to implant the prosthesis 1700. The net result is that the beveled end and marker permits superior alignment that helps reduce tilting, or canting, of the prosthesis during implantation. This reduced canting is further aided by the flexibility of the distal end of member 118.

FIG. 21B illustrates the prosthesis 1700 in a semi-collapsed state, showing the rotation of the paddle (at upper right) from a radial outward orientation toward an axial orientation to match the orientation of the proximal face of the distal disc. FIG. 21C shows the prosthesis 1700 partially drawn proximally into the distal tip 122 of the delivery catheter, whereas FIG. 21D shows the prosthesis fully withdrawn proximally into the delivery catheter. Finally, FIG. 21E shows the lateral orientation of the delivery system and prosthesis as it is envisioned in use during the implantation procedure, with the paddle extending upwardly in an orientation where it can contact the arterial wall above the access opening.

Figure 22:
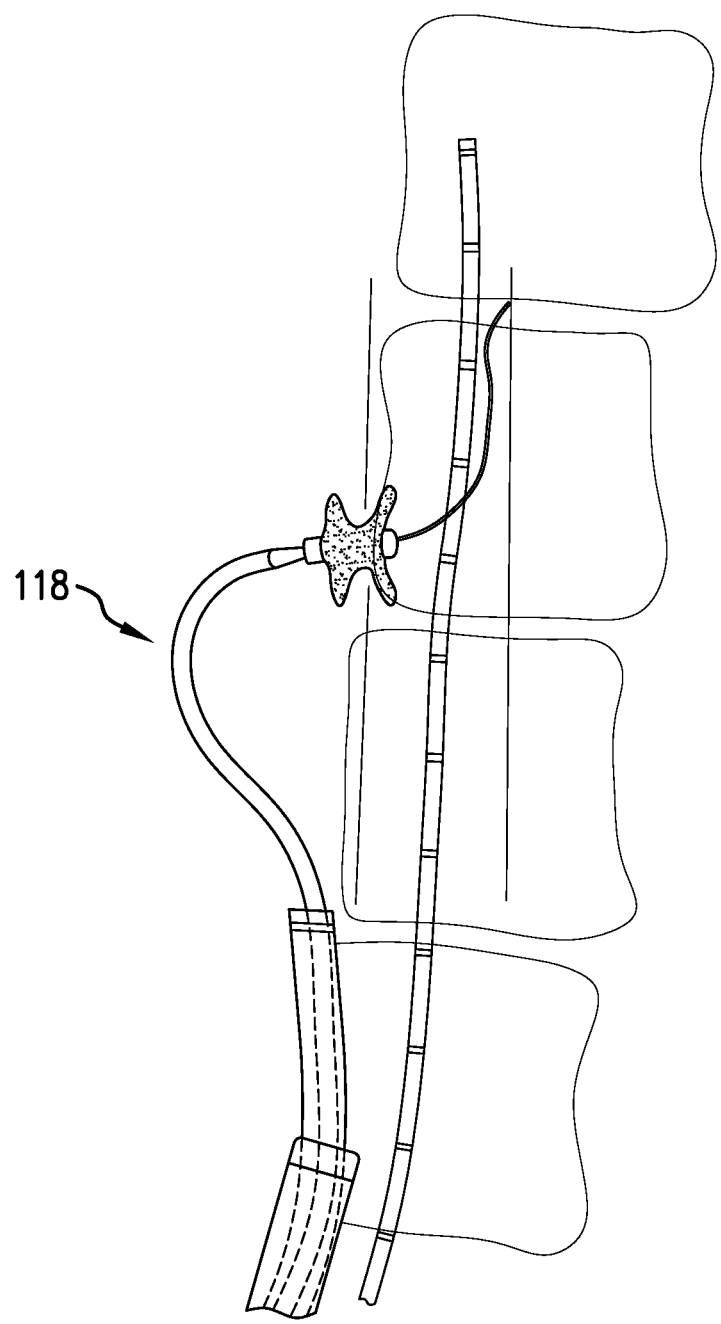

FIG. 22 illustrates placement of the disclosed system in situ in actual use, wherein the delivery catheter is advanced through the inferior vena cava, and the guidewire and prosthesis extend into the abdominal aorta. As illustrated, portion 118 of the delivery system is permitted to flex into the disclosed reverse question mark shape, facilitating alignment and placement of the prosthesis 1700 by rotating the prosthesis about the paddle that is urged against the arterial wall above the access opening into the abdominal aorta. Also pointed out are the location of the marker at the base of the paddle, as well as the marker on the beveled tip 122 of the delivery catheter.

In further accordance with the disclosure, embodiments are also provided, but not specifically illustrated, that adds the tethering features of the embodiments of FIGS. 14-17 to any other embodiment disclosed herein, including but not limited to the embodiments of any of FIGS. 1-13, whether or not such embodiments are constructed with a resilient member or coil spring.

In further accordance with the disclosure, any prosthesis disclosed herein can be formed at least in part from a composite wire. In some embodiments, the composite wire can be drawn filled wire. For example, the drawn filled wire can include a first material, and a second material in a different region of the drawn filled wire that has greater radiopacity than the first material. The first and second materials can include metallic components and/or bioresorbable components. If desired, the second material can be located along a core region of the wire, and first material can surround or substantially surround the first material. The first material can include a NiTi alloy, and the second material can include platinum, for example. Other suitable examples for making such composite materials can be found in U.S. patent application Ser. No. 10/524,387, filed Sep. 13, 2004, which is incorporated by reference herein in its entirety for any purpose whatsoever.

The devices disclosed herein can be implanted via the delivery system in transmural or transcameral applications using techniques similar to those presented in International Patent Application No. PCT/US2013/072344, filed Nov. 27, 2013 and published Feb. 12, 2015 as WO/2015/020682 A1, which is incorporated by reference herein in its entirety for any purpose whatsoever. However, the presently disclosed embodiments permit easier deployment, adjustment, and retrievability by virtue of the elastic member and pushrod, among other things.

Thus, an exemplary method for use of any of the devices herein can be in conjunction with a method of transcatheter delivery of a device to the cardiovascular system. The method can include advancing a puncture device through a femoral vein to a venous crossing site, the venous crossing site being located along an iliac vein or the inferior vena cava. The method can further include using the puncture device to puncture a venous wall at the venous crossing site and then puncture an adjacent arterial wall at an arterial crossing site. The arterial crossing site is preferably located along an iliac artery or the abdominal aorta. The method can further include advancing at least a portion of the puncture device into the iliac artery or the abdominal aorta, thereby forming an access tract between the venous crossing site and the arterial crossing site.

The method can further include advancing a catheter through the access tract from the venous crossing site to the arterial crossing site, and delivering the device into the iliac artery or the abdominal aorta through the catheter. The device can be a prosthetic heart valve, aortic endograft, left ventricular assist device, or cardiopulmonary bypass device among other potential devices. In some embodiments, the puncture device can be selectively electrically energized to puncture the venous wall and the arterial wall. The puncture device can include inner and outer coaxial members, wherein the inner member comprises a guide wire or needle that is advanced to initially puncture the venous and arterial walls, and the outer member can be advanced over the inner member to enlarge the initial punctures and facilitate introduction of larger devices through the access tract. A target device can be advanced through a peripheral artery to adjacent the arterial crossing site. The target device can be used to guide an operator in directing the path of the puncture device through the arterial wall and into the iliac artery or the abdominal aorta.

After the access tract is formed, a guidewire can be introduced through the access tract. The catheter can then be advanced over the guidewire through the access tract into the iliac artery or the abdominal aorta to deliver the device. After delivering the device, an occlusion device as described herein can be delivered over a guidewire into the access tract to close the access tract. The occlusion device is preferably radially compressible for transcatheter delivery and radially expandable for implantation. The occlusion device can include an arterial portion for placement at the arterial crossing site, a venous portion for placement at the venous crossing site, and a neck portion for placement in the access tract. The occlusion device can include a guidewire channel extending through the venous portion, the neck portion, and the arterial portion. This portion of the procedure can be implemented by deploying a delivery catheter as disclosed herein and advancing it into the artery and deploying a first portion, such as a lobe or disc, of the prosthesis into the artery, optionally deploying one or more discs between the artery and vein, and deploying a disc or lobe into the vein. If the prosthesis includes a spring as described herein or tethers, the device can be collapsed by pushing on the push rod to partially collapse the prosthesis to permit it to be repositioned and redeployed, or fully collapsed and withdrawn back into the delivery system. The implant is preferably configured to be implanted across an arteriovenous fistula or tract connection between an artery and a vein with the arterial end portion positioned in the artery, wherein the venous end portion is positioned in the vein, and a neck portion is positioned in the fistula or tract connection.

The systems disclosed herein can be used to close congenital heart defects including atrial septal defect, ventricular septal defect, persistently patent ductus arteriosus. The system can be used to closed iatrogenic heart defects including extra-anatomic vascular access ports from the chest across the wall of the left or right ventricle into the respective lumen, or from the chest across the wall of the left or right atrium into the respective lumen, both to achieve temporary transcatheter access to the heart to allow therapeutic catheter interventional procedures or implantation such as mitral valve or tricuspid valve or aortic valve or pulmonic valve or prosthesis or annuloplasty implantation or modification or repair of Paravalvular leaks.

All statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

The methods and systems of the present disclosure, as described above and shown in the drawings, provide for improved techniques for treating lumenal systems of patients. It will be apparent to those skilled in the art that various modifications and variations can be made in the devices, methods and systems of the present disclosure without departing from the spirit or scope of the disclosure. Thus, it is intended that the present disclosure include modifications and variations that are within the scope of the subject disclosure and equivalents.

What is claimed is:

1. An axially telescoping prosthesis comprising:
    a) a plurality of discrete radially expandable braided mesh bodies, each of said bodies being formed from a plurality of filaments that can slide across one another, each of the braided mesh bodies being configured to self-expand into at least one disc, each radially expandable braided mesh body defining a volume therein, the plurality of mesh bodies being axially displaceable with respect to one another; and
    b) a resilient member structurally distinct from the plurality of discrete mesh bodies, the resilient member being attached to and arranged to pass through a central region of the mesh bodies, the resilient member being configured and arranged to attach the plurality of discrete radially expandable braided mesh bodies to each other, wherein: (i) the radially expandable braided mesh bodies are selectively telescopically displaceable from one another along a central longitudinal axis of the prosthesis by stretching or relaxing the resilient member to accommodate differently sized anatomies, (ii) the resilient member is substantially co-axial with the central longitudinal axis of the prosthesis, and (iii) the resilient member is configured to cause the prosthesis to shorten along the axis and expand radially when the resilient member is relaxed.

2. The prosthesis of claim 1, further comprising at least one length limiting tether attaching the plurality of discrete radially expandable braided mesh bodies to each other, the at least one length limiting tether acting to prevent the resilient member from elongating beyond a predetermined length.

3. The prosthesis of claim 1, further comprising (i) at least one fabric disc disposed within each of the radially expandable mesh bodies; and (ii) a tubular fabric portion attached to at least one of the fabric discs, the tubular fabric portion extending proximally into a neck region of the prosthesis.

4. The prosthesis of claim 1, wherein the resilient member is a coil spring surrounded by fabric that causes the prosthesis to collapse axially and the radially expandable braided mesh bodies to expand radially and is configured to prevent the prosthesis from being pulled axially through an anatomical opening it has been delivered through after it has been deployed, and further wherein a neck region of the prosthesis spanning between the radially expandable braided mesh bodies including the coil spring surrounded by the fabric expands radially outwardly when the coil spring is unconstrained to help achieve hemostasis.

5. The prosthesis of claim 1, wherein the resilient member is a tension coil spring.

6. The prosthesis of claim 1, wherein the prosthesis defines a lumen along its length through the plurality of discrete radially expandable braided mesh bodies along an axial centerline of the prosthesis, the lumen being configured and arranged to act as an adjustable shunt having an adjustable length when the prosthesis is deployed to connect two lumens.

7. The prosthesis of claim 1, wherein the prosthesis is configured to seal at least one hole in one lumen.

8. A system for delivering a prosthesis according to claim 1, comprising:
 a) an outer tubular sheath having a proximal end and a distal end and defining a first lumen therethrough along at least a portion of its length;
 b) an intermediate tubular member disposed at least partially within the first lumen and being slidably disposed with respect to the outer tubular sheath, the intermediate tubular member having a proximal end, a distal end, and, a flexible distal portion configured to be protrudable distally beyond the distal end of the outer tubular sheath, the intermediate tubular member defining a second lumen therethrough along at least a part of its length;
 c) an inner elongate member being disposed at least partially within the second lumen, the inner elongate member being slidably disposed with respect to the intermediate tubular member, the inner elongate member having a proximal end and a distal end configured to be displaced distally beyond the distal end of the intermediate tubular member; and
 d) a prosthesis according to claim 1 removably mounted on the distal end of the intermediate tubular member, wherein the prosthesis can be longitudinally stretched by advancing the inner elongate member distally with respect to the intermediate tubular member and against an inner face of an end region of the prosthesis, and further wherein said longitudinal stretch of said prosthesis causes the prosthesis to collapse radially inwardly to permit said prosthesis to be withdrawn into said distal end of said outer tubular sheath.

9. The system of claim 8, wherein the distal end of the outer tubular member is cut at an angle that is oblique with respect to a central axis defined by the system.

10. The system of claim 9, wherein the distal end further includes a radiopaque marker proximate the distal end making the angle at which the distal end is cut being visible under fluoroscopy to help reduce canting of the prosthesis during implantation.

11. The system of claim 8, wherein the flexible of distal portion of the intermediate tubular member is configured and adapted to permit the intermediate tubular member to be deformed into a reverse curved geometry with respect to a central axis of a proximal portion of the delivery system while inside a patient's lumen.

12. The system of claim 8, wherein the inner elongate member is a tubular member configured to permit a guidewire to pass therethrough.

13. The system of claim 12, wherein the distal end of the inner elongate member is configured to abut against the inner face of the end region of the prosthesis to form a guidewire lumen to permit the guidewire passing through the inner elongate member to pass through a distal face of the prosthesis.

* * * * *